(12) United States Patent
Shin et al.

(10) Patent No.: US 8,293,515 B2
(45) Date of Patent: Oct. 23, 2012

(54) ***SALMONELLA* BACTERIOPHAGE AND ANTIBACTERIAL COMPOSITION COMPRISING THE SAME**

(75) Inventors: Soo An Shin, Seoul (KR); Min Tae Park, Seoul (KR); Hyang Choi, Anyang-si (KR); Young Wook Cho, Seoul (KR); In Hye Kang, Suwon-si (KR); Su Jin Choi, Daegu (KR)

(73) Assignee: CJ Cheijedang Corporation, Seoul (KR)

( * ) Notice: Subject to any disclaimer, the term of this patent is extended or adjusted under 35 U.S.C. 154(b) by 0 days.

(21) Appl. No.: 12/875,863

(22) Filed: Sep. 3, 2010

(65) Prior Publication Data

US 2011/0052542 A1 Mar. 3, 2011

Related U.S. Application Data

(60) Provisional application No. 61/239,751, filed on Sep. 3, 2009.

(51) Int. Cl.
*C12N 7/00* (2006.01)
(52) U.S. Cl. .................................. 435/235.1
(58) Field of Classification Search .................. None
See application file for complete search history.

(56) References Cited

U.S. PATENT DOCUMENTS

| | | | |
|---|---|---|---|
| 6,485,902 B2 | 11/2002 | Waddell et al. | |
| 6,942,858 B1 | 9/2005 | Ghanbari et al. | |
| 2004/0208853 A1* | 10/2004 | Sulakvelidze et al. | 424/93.6 |

OTHER PUBLICATIONS

Al-Tarazi et al., Asian-Aust. J. Anim. Sci., 2003, 16(1):77-82.*
Raya et al., Applied and Environmental Microbiology, 1989, 55(9):2206-2213.*
O'Flynn et al., Journal of Applied Microbiology, 2006, 101:251-259.*
Barrangou et al., Applied and Environmental Microbiology, 2002, 68(11):5452-5458.*
Goto et al., J. Food Hyg. Soc. Japan, 2004, 45(1):25-28.*
Zoonoses Report, 2003, pp. 1-71, United Kingdom.

* cited by examiner

*Primary Examiner* — Zachariah Lucas
*Assistant Examiner* — Nicole Kinsey White
(74) *Attorney, Agent, or Firm* — Knobbe, Martens, Olson & Bear, LLP

(57) ABSTRACT

Disclosed herein is a novel bacteriophage which has specific bactericidal activity against one or more *Salmonella* bacteria selected from the group consisting of *Salmonella Enteritidis, Salmonella Typhimurium, Salmonella Gallinarum*, and *Salmonella Pullorum* without affecting beneficial bacteria, in addition to showing excellent tolerance to acid, heat and desiccation. The novel bacteriophage can be widely used as an active ingredient for therapeutic agents, animal feeds or drinking water, cleaners and sanitizers for preventing and treating the infectious diseases caused by *Salmonella Enteritidis, Salmonella Typhimurium, Salmonella Gallinarum* or *Salmonella Pullorum* including salmonellosis, *Salmonella* food poisoning, Fowl Typhoid, and Pullorum disease or for controlling the *salmonella* bacteria.

8 Claims, 8 Drawing Sheets

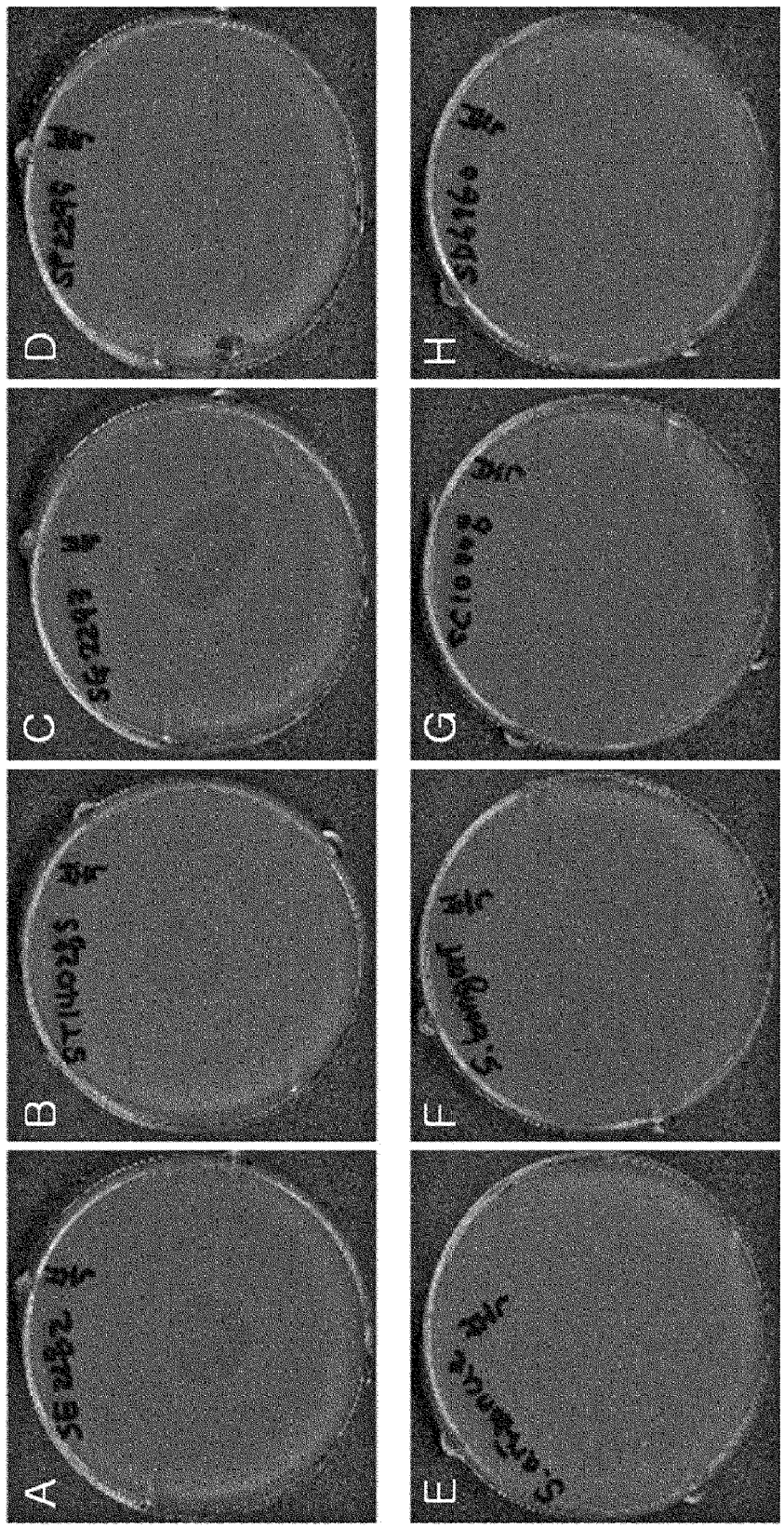
[Figure 1]

【Figure 2】
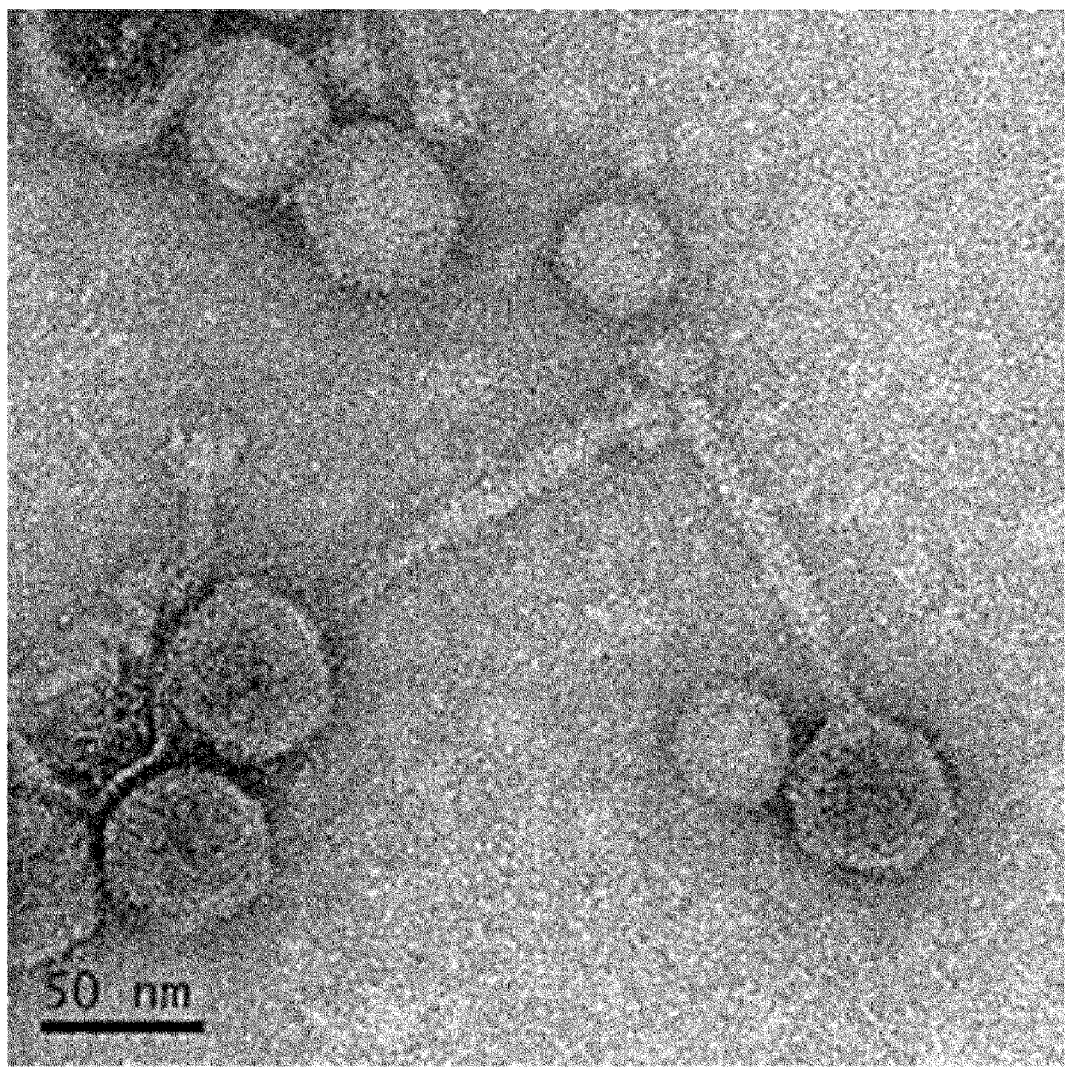

【Figure 3】
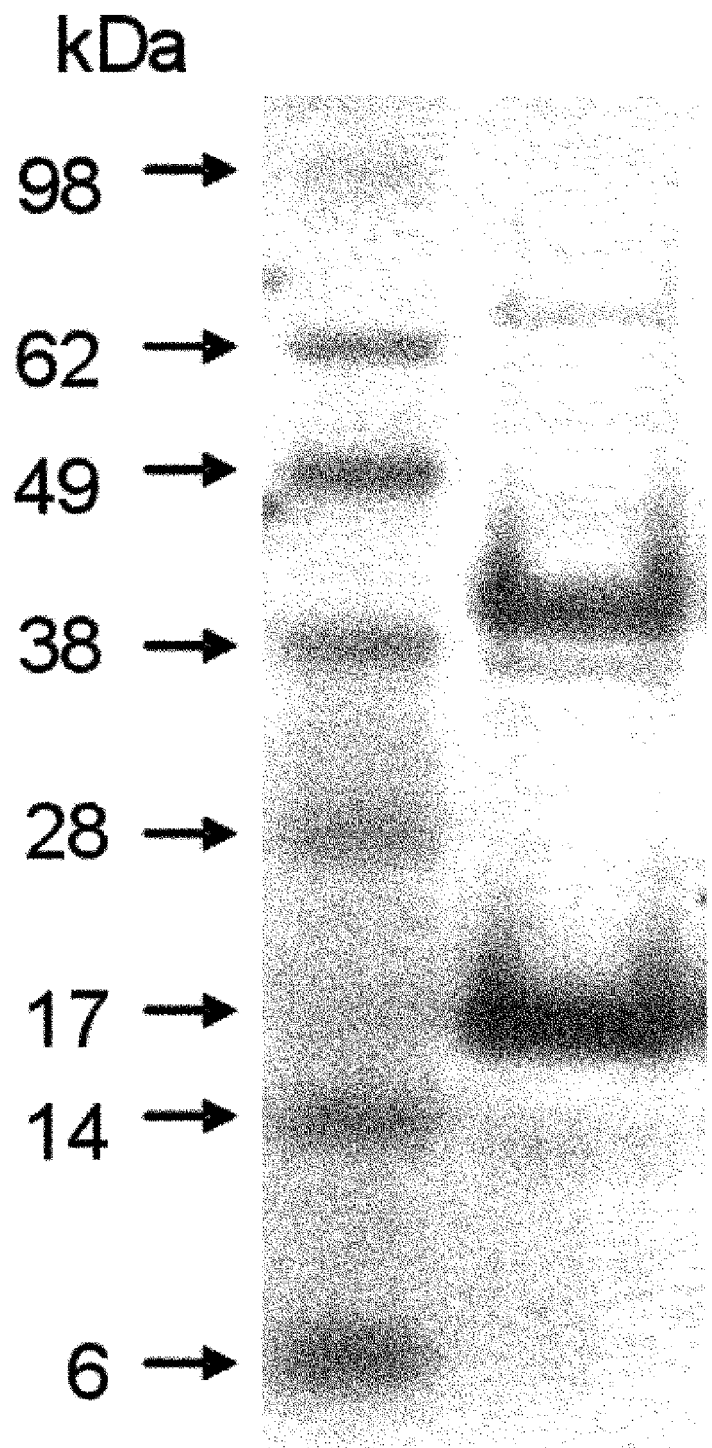

[Figure 4]
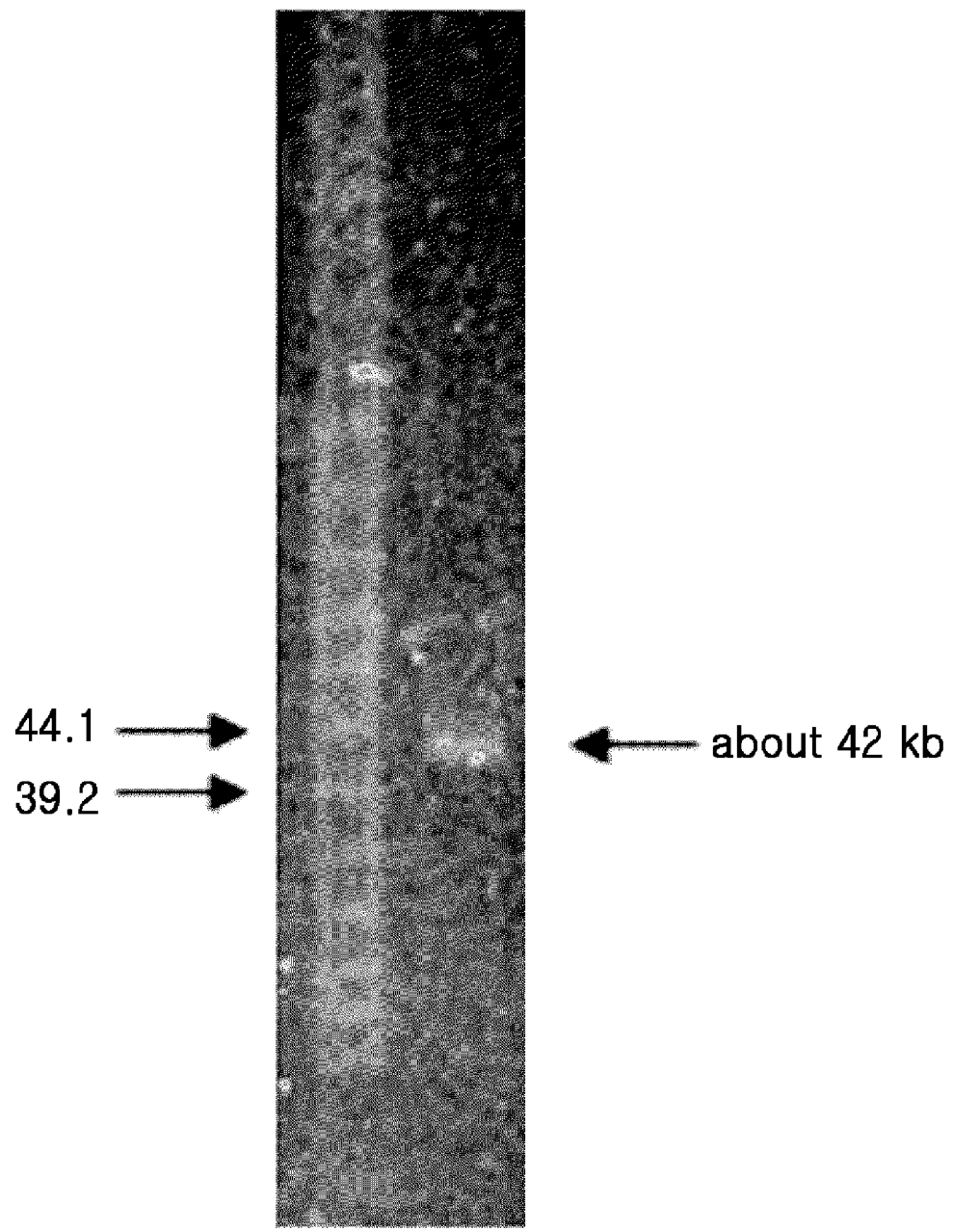

[Figure 5]
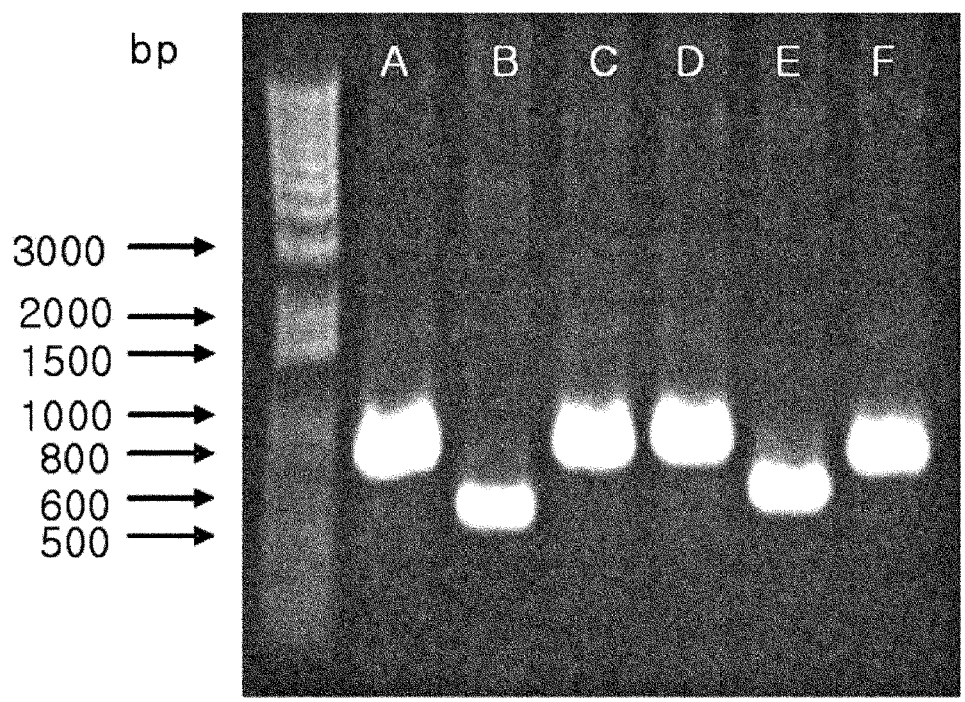
[Figure 6]
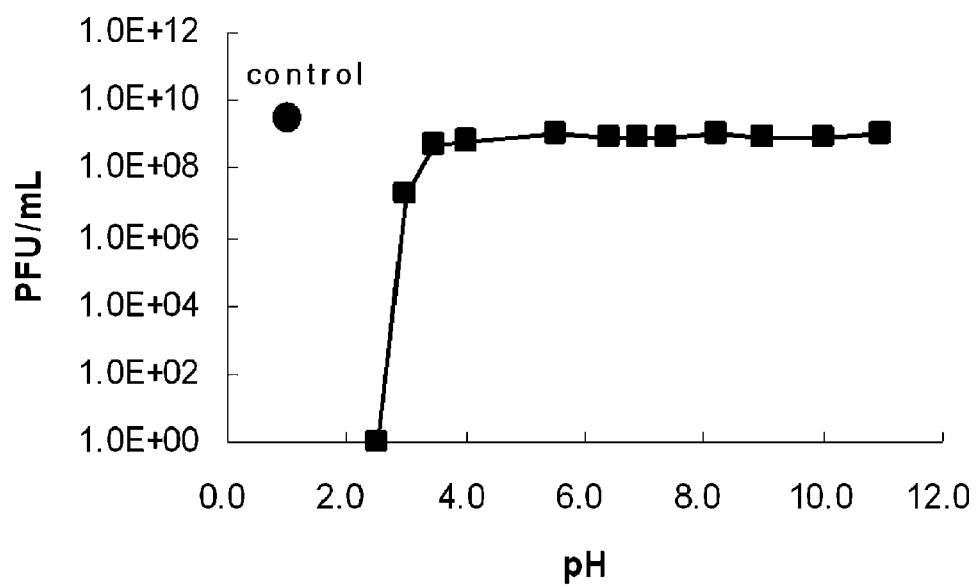

[Figure 7]
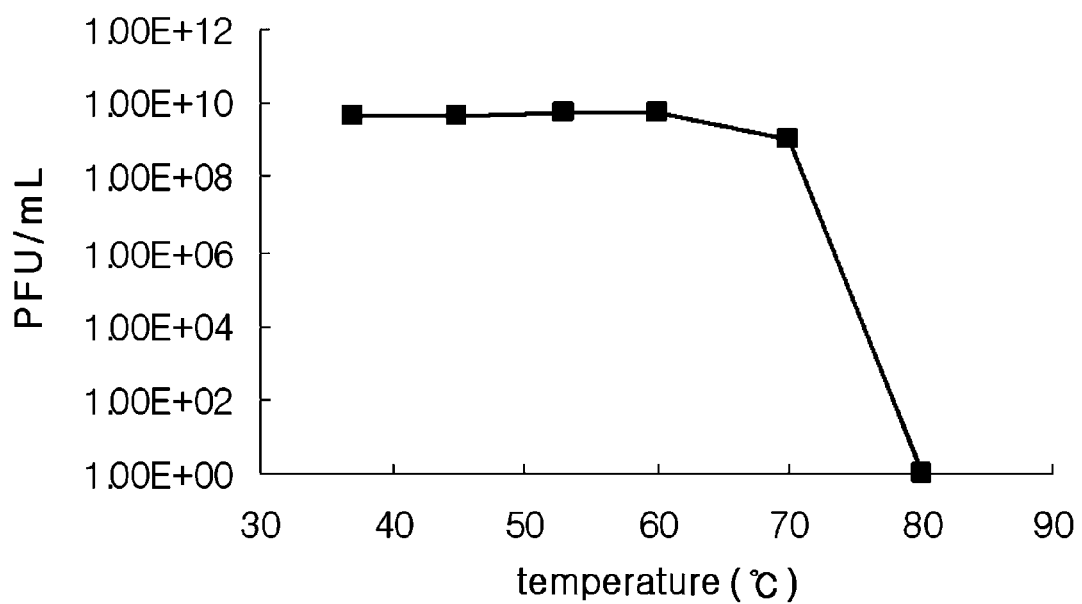

[Figure 8]
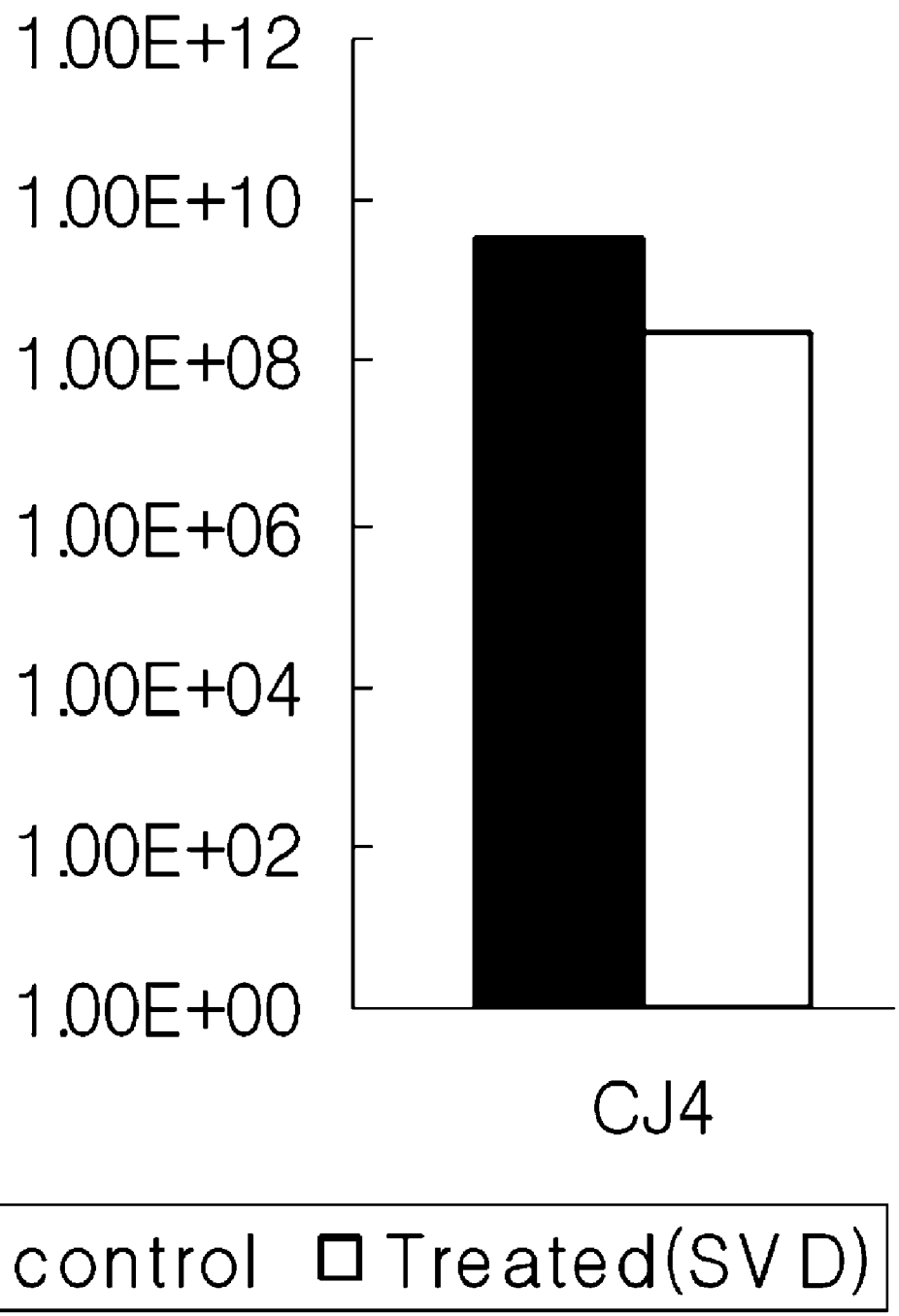

[Figure 9]
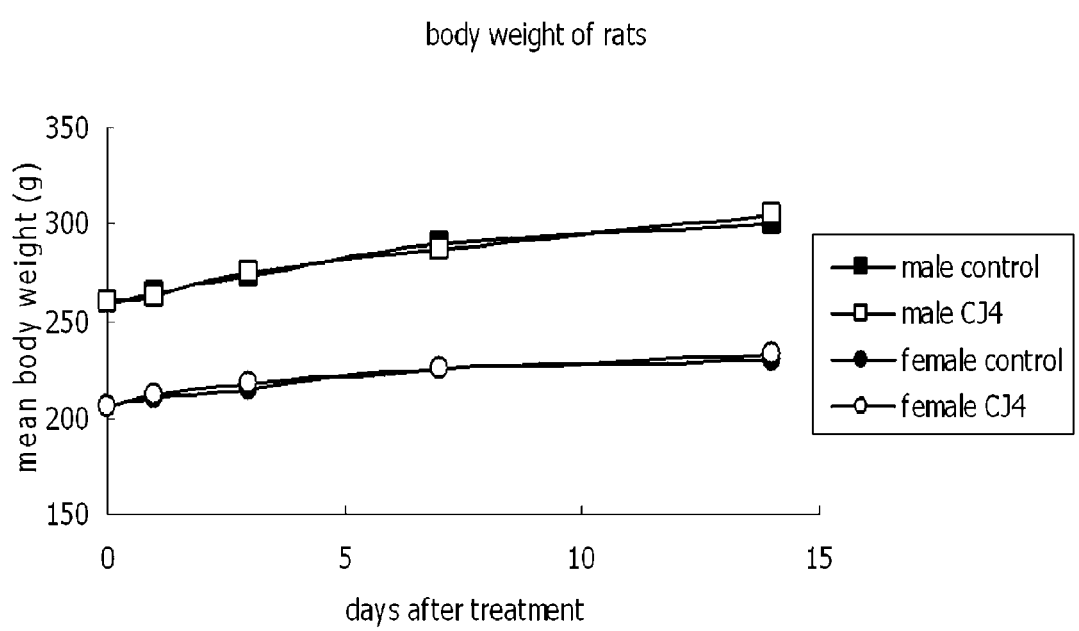

SEQUENCE LISTING

<160> NUMBER OF SEQ ID NOS: 20

<210> SEQ ID NO 1
<211> LENGTH: 1029
<212> TYPE: DNA
<213> ORGANISM: Bacteriophage KCCM11027P

<400> SEQUENCE: 1
atctcctcaa cataggcaac gttaacttcg ccggggcgat ggctgaccag gctaatacccc    60

```
tgaacggagc tatcgctagt gcggaggact catggtccca gttgaagatg actctcgcta      120
ctagtctgga tgtagggtcg ctggcggaac ctttacgtta tattgacgac ctgatacagg      180
agataaacgc tcaggtcgca tccggtgagt tcgtagccga gatgcagatg tggggtgaca      240
tggcatccga tgttgggggt gcgatagagg cttcattcga cgcggcgttt gggacggttg      300
cagacgcgtt aaacgctttg aactccgcct ggacttacac cagtgaaagc attaccggaa      360
gcggagagga gaccgcatct acgatagctg agtcggcggc ggatgcgctg gacttcattg      420
cccaggaatt tacagcaatg gagcggtttt ttgaagatat ggttaaaggt gctcaggatg      480
caggacgtct tgtaaaggcc gccttgacgc cgggagagtc ggtagctgag gccaagaacc      540
ttaacttcca gttagcgctt gctatggata ctcaaagggg tgtggctgac ctgacacgga      600
aaagtttccg cgaacaagta gaagctcagg aagaccttat tgcgctgaag cgagcggctt      660
acgacatcga tgaagaagca gctaaggccg aggggttagg taagtttaag gtatcaggta      720
cggacagcgg ttctacaggt gattccgcag acaaggccgc taagaaatcc gtcgacgcat      780
tcgaacgcca aagaaagcc gctgaggatt tctattatca gtcaatccac cttaacgacg      840
acgtattcca gagatacaag ctaaccaaga gagcaacttt acaaagctac aggagttcta      900
cagcaaccgt ctccttagtg accagcatac gaaaccgcga agacgcagat tatgctcgag      960
gcggatacgg ccgccaggct gagtagataa cgcgagaaag aacgctggaa aaacagttct     1020
cgcgatgcg                                                             1029

<210> SEQ ID NO 2
<211> LENGTH: 741
<212> TYPE: DNA
<213> ORGANISM: Bacteriophage KCCM11027P

<400> SEQUENCE: 2
cgaacgccgt cgtaaccgtt aatatatttt cttttcaatt aaggcggctt cggtcgcctt       60
ttctataagg gtcaaataaa tgaatctgct ttatctcgat actgaaacat tttcagaagc      120
cgatttaaaa aaagtcggtt cctatgctta cgccgaacat ccgactaccg aaattgttat      180
ctgcacctac gctttcgatg aaggccctgt gcaagtatgg gacgccaccg acggcagcga      240
tatgccgcgt gatttgcgtc gggcgatgtt gaagctgcaa aaaccagaca gcaatctcaa      300
actggtaggc caaaacttcc ttatgttcga ccgaccagtt attaagcatt gctggggtt       360 cgaactcctg gtagaaaaca ttatagacac tatgatagta gcgttccgac atgccctccc      420
gggttcactg gccgcgctgt gtgaggtttt aaacattgac gcaagcatgg ctaaggataa      480
acgtggtaag gcgctgatac agcgattcag taagcctacg cccaagaact ataagattcg      540
acgttatact gccgataccc acccaaaaga gtgggcagaa tttattgcat acgcaaaaag      600
cgactttacg tccatgcgtg aagtgtataa gaaaatgcct aactgggtga attctgagtt      660
cgaaaaccgc gtgcggcact taaacgggc gattaattac cgaggattaa aggtgttgtg      720
gctttgctgg aagcggtaaa g                                               741

<210> SEQ ID NO 3
<211> LENGTH: 997
<212> TYPE: DNA
<213> ORGANISM: Bacteriophage KCCM11027P

<400> SEQUENCE: 3
atctcctcaa cataggcaac gttaacttcg ccggggcgat ggctgaccag gctaataccc       60
tgaacggagc tatcgctagt gcggaggact catggtccca gttgaagatg actctcgcta      120
```

```
ctagtctgga tgtagggtcg ctggcggaac ctttacgtta tattgacgac ctgatacagg    180
agataaacgc tcaggtcgca tccggtgagt tcgtagccga gatgcagatg tggggtgaca    240
tggcatccga tgttgggggt gcgatagagg cttcattcga cgcggcgttt gggacggttg    300
cagacgcgtt aaacgctttg aactccgcct ggacttacac cagtgaaagc attaccggaa    360
gcggagagga gaccgcatct acgatagctg agtcggcggc ggatgcgctg gacttcattg    420
cccaggaatt tacagcaatg gagcggtttt ttgaagatat ggttaaaggt gctcaggatg    480
caggacgtct tgtaaaggcc gccttgacgc cgggagagtc ggtagctgag gccaagaacc    540
ttaacttcca gttagcgctt gctatggata ctcaaagggg tgtggctgac ctgacacgga    600
aaagtttccg cgaacaagta gaagctcagg aagaccttat tgcgctgaag cgagcggctt    660
acgacatcga tgaagaagca gctaaggccg aggggttagg taagtttaag gtatcaggta    720
cggacagcgg ttctacaggt gattccgcag acaaggccgc taagaaatcc gtcgacgcat    780
tcgaacgcca gaagaaagcc gctgaggatt tctattatca gtcaatccac cttaacgacg    840
acgtattcca gaagatacaa gctaaccaag agcaacttt acaaagctac aggagttcta    900
cagcaaccgt ctccttagtg accagcaata cgaaaccgcg aagacgcaga tatgcctcga    960
ggcggatacg gccgccaggc tgagttagat aacgcga                            997

<210> SEQ ID NO 4
<211> LENGTH: 969
<212> TYPE: DNA
<213> ORGANISM: Bacteriophage KCCM11027P

<400> SEQUENCE: 4
aacggtctca ttgttgctga agttgtaatc gcggtcgata agaacactat caacagcggc     60
atccgccaat cgttgtaacg tagtaaagtc agacagctta acggagtact taaatttctt    120
atccgcttcc gcacggaagg tgatgtcccc aaaaagctacc caagcagaat cagaaatgcc    180
accggttgtt agagggtag acgccgcggg gataactttc ggcagggagc cacgccatgc    240
gtaatagtta ccgtccccgc catcttcttt cggccaaaga accgctttat tggcgtcgtt    300
aattcccagg gttccgccgg ttgtgaagtt aaaagacgcc ggagagaaac cggcgtcacg    360
caagaccgcg ggcagcgtct tctgcgtctg cccggttacc tggttagtag cgtagtcgat    420
atctgcgcca cccgctacac caccctgtct gccggtgatc acctcggctt cgaaaatctg    480 gtgttttta gctacctgta aatcgtaaag tgacaataca tcaccgcaac cactagacat    540
atgactatcc tcttagttaa aaccgttatc gaatccgtta gagaacgcac gaccgaaagg    600
cggtacgttg tcgaacttat agaaatcctt gtcatagtta aacccggtta ttttgactgt    660
tctgtcatcg ccggggtcta ccgtagaaac aagaatcatc tgagcattat gccttgcttc    720
gttgccgaat gaaaattcag ttttcagggc gctattaccc gtgtaaatgg cttcctgcgg    780
tacagaagtc ataatcaccc gcctgtcgtg cgctccaggg actacattaa cactttgcac    840
gccgccgtca cgtaacttga gaatcaaaga atggtcatct cccgaggtga acttaactgg    900
gttgtgacag ttctacgtga gcccgtttac cgcggttacg tagccgtcgt agtcgcatac    960
gtgaaccct                                                            969

<210> SEQ ID NO 5
<211> LENGTH: 918
<212> TYPE: DNA
<213> ORGANISM: Bacteriophage KCCM11027P

<400> SEQUENCE: 5
```

```
gacgtagaga taataggaca ctattaacgg ttatgcaagc tattttgtta ttcttatttg    60
gcgtctacgg tcgcaccgga aaagcgggtg gttcccgcct ggtgcaacta ccaaccagta   120
accgactaac caaagggcat tactatgaaa cttagcgatt tttactacga agccgaagcc   180
gagaaaggcg cgcgcatgcc gattcctttα aaagatggta cagattcagg agaatggttg   240
aacgttgtct ccccggaggc cgatgtcgcg gttaaagcta tgcgtgcctt caccctggcg   300
taccgagcgg cggtaggtaa attaaaaccg cttcgggata aatgcgaaga gcaaaaagac   360
ttctcagaat acaatttaaa aatggaagac gcggcaggag acctaaaccg acaattggct   420
ctcgaattgg tgaatggctg gagtctcgat gatgagttca ctaaggaaaa tcttaagact   480
cttctcaccc aatataagcg cctggcggaa catgtagtcg tattccacca cgaacagttg   540
cgtcaattgc aggaaaagta gacgcgttgt ttcagtttgc ccgttggaac ttcataaccc   600
gccacgaaag gcgcaagttt gacagtatcg ccgatgggca caaagccgcg cttatcgcta   660
tgggggtaat aaaagacgcg ggagaaacaa cgcaggacgc cgggcctgaa tgcccccctg   720
aactactcac cacttttgag aagtatcgtg atgttaaatt cacccgccgc gttgatgacg   780
acggcgtaaa gctataccca agagagcaac ttagttggtc agatttagtg gcgtatagca   840
ctatttcagg tcagatatag ggatgtttga atctgaaatt atcatgggct tagacgccat   900
ttttgagggt agaaacga                                                  918

<210> SEQ ID NO 6
<211> LENGTH: 1004
<212> TYPE: DNA
<213> ORGANISM: Bacteriophage KCCM11027P

<400> SEQUENCE: 6
aacttatacg ggcaaacacg tgacaacacc ccacactacg gcaacagaac aacagtacac    60
tcgatgcgca agcagacccc acgtgctgcg gaagtaaagc aaccacagtt acgtatgatt   120
gccaccgaaa tggtacacaa ataccttggt aacggtgttt tcgaagatac gatgaccccc   180
aatacccagg ccgtgcaatc tcttatccgc ctggcgcgtg atccggatgt gggggggttta   240 aacctgacgg tacgcaacat ggataagtta cttgccgtgc agaacgaggt cgaagcgtat   300
ttcggtgaca acaggctgg agaattttgt tacacgtttg atgactataa aaccactatg   360
caggatatag ttagtactat agccgacgct atcttctgta ctccatatag gcgtggggcg   420
gatatccttc tcgattttga acgccctcgc atgggccctg agatggtgtt cacccaccga   480
agcaaggctg gtacttccga aaaatggacc agaaccttta acgatgctca ggtgttcgat   540
agccttaaat tctcgtacat agacccaaaa acaaacgtta agaaacaat aacaatacca   600 gaaactggtg gggttaaaac ggagacctac gattcaaaag gtattcgcaa ctataagcag   660
gctttctggg cagcgcaccg ccgccaccag aagaacattt taaagaaaat ttcagtgtcg   720
tttaccgcca cggaagaggg tatctttgct ttaccaaatc gtgccattag tgtggttaag   780
ggttcacgta tggcgaccta cgacggctac gtaaccgcgg taaacgggct caccgtagaa   840
ctgtcacaac cagttaagtt caccctcggga gatgaccatt ctttgattct caagttacgt   900
gacggcggcg tgcaaagtgt taatgtagtc cctggagcgc acgacaggcg ggtgattatg   960
acttctgtac cgcaggaagc catttacacg ggtatagcgc cctg                   1004

<210> SEQ ID NO 7
<211> LENGTH: 18
<212> TYPE: DNA
<213> ORGANISM: Artificial Sequence
```

```
<220> FEATURE:
<223> OTHER INFORMATION: primer

<400> SEQUENCE: 7
cctgaacgga gctatcgc                                                 18

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ggagacggtt gctgtagaac                                               20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
atctgcttta tctcgatact                                               20

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
cccgtttaag tgccgcac                                                 18

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
tcctcaacat aggcaacg                                                 18

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
aggagacggt tgctgtagaa                                               20

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
aacggtctca ttgttgctg                                                19
```

-continued

```
<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14
gacggctacg taaccgcg                                                 18

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
gattccttta aaagatggt                                                19

<210> SEQ ID NO 16
<211> LENGTH: 18
<212> TYPE: DNA
<213> ORGANISM: Artificial Sequence
<220> FEATURE:
<223> OTHER INFORMATION: primer

<400> SEQUENCE: 16
atggcgtcta agcccatg                                                 18

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ccacactacg gcaacagaac                                               20

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
cgccgtcacg taacttgag                                                19

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
cgggcctctt cgctattac                                                19

<210> SEQ ID NO 20
<211> LENGTH: 20
<212> TYPE: DNA
```

```
<213> ORGANISM: Artificial Sequence
<220> FEATURE:
<223> OTHER INFORMATION: primer

<400> SEQUENCE: 20
aggcttaccc gtcttactgt                                                   20
```

SALMONELLA BACTERIOPHAGE AND ANTIBACTERIAL COMPOSITION COMPRISING THE SAME

CROSS-REFERENCE TO RELATED PATENT APPLICATION

This application claims the benefit of U.S. Provisional Application No. 61/239,751 filed on Sep. 3, 2009, the disclosure of which is hereby expressly incorporated by reference in its entirety and hereby expressly made a portion of this application.

TECHNICAL FIELD

The present invention relates to a novel bacteriophage and antibacterial composition comprising the same.

BACKGROUND ART

*Salmonella* is a genus of the family Enterobacteriaceae, characterized as Gram-negative, facultatively anaerobic, non spore-forming, rod-shaped bacteria, and most strains are motile by flagella. *Salmonella* has an average genomic GC content of 50-52%, which is similar to that of *Escherichia coli* and *Shigella*. The genus *Salmonella* is a pathogenic microorganism that causes infections in livestock as well as in humans. Serological division has it that *Salmonella enterica*, a species of *Salmonella* bacterium, has a variety of serovars including *Gallinarum, Pullorum, Typhimurium, Enteritidis, Typhi, Choleraesuis*, and *derby* (Bopp C A, Brenner F W, Wells J G, Strokebine N A. *Escherichia, Shigella, Salmonella*. In Murry P R, Baron E J, et al., eds. *Manual of Clinical Microbiology*. 7th ed. Washington D.C. American Society for Microbiology 1999; 467-74; Ryan K J. Ray C G (editors) (2004). *Sherris Medical Microbiology* (4th ed). McGraw Hill. ISBN 0-8385-8529-9.). Of them, *Salmonella Gallinarum* and *Pullorum* are fowl-adapted pathogens, *Salmonella Typhi* is a human-adapted pathogen, *Salmonella Choleraesuis* and *Salmonella derby* are swine-adapted pathogens, and *Salmonella Enteritis* and *Salmonella Typhimurium* are pathogenic for humans and animals. Each serovar causes illness in the respective species, resulting in tremendous damage to farmers or consumers.

A disease of domestic birds caused by *Salmonella* bacterium is Fowl Typhoid (FT), which is caused by a pathogen, *Salmonella Gallinarum* (hereinafter, referred to as "SG"). Fowl Typhoid (FT) is a septicemic disease of domestic birds such as chicken and turkey, and the course may be acute or chronic with high mortality. A recent report has had it that Fowl Typhoid frequently occurs in Europe, South America, Africa, and Southeast Asia, with damages increasing every year. Outbreaks of FT in South Korea have been reported since 1992 and economic losses caused by FT in brown, egg-laying chickens are very serious (Kwon Yong-Kook. 2000 annual report on avian diseases. Information publication by National Veterinary Research & Quarantine Service. March, 2001; Kim Ae-Ran et al., The prevalence of pullorum disease-fowl typhoid in grandparent stock and parent stock in Korea, 2003, Korean J Vet Res (2006) 46(4): 347~353).

Pullorum disease is also caused by a strain of the *Salmonella* bacteria, *Salmonella Pullorum* (hereinafter, referred to as "SP"). Pullorum disease occurs in any age or season, but young chickens are particularly susceptible to the disease. During the past century, it has been a serious disease among young chickens at 1-2 weeks of age or younger. Since the 1980s, the occurrence has greatly decreased. However, it has been growing since the mid-1990s (Kwon Yong-Kook. 2000 annual report on avian diseases. Information publication by National Veterinary Research & Quarantine Service. March, 2001; Kim Ae-Ran et al., The prevalence of pullorum disease-fowl typhoid in grandparent stock and parent stock in Korea, 2003, Korean J Vet Res (2006) 46(4): 347~353).

In South Korea, outbreaks of Fowl Typhoid and Pullorum disease have been increasing since the 1990s, inflicting economic damages on farmers. For this reason, a live attenuated SG vaccine has been used in broilers for the prevention of Fowl Typhoid from 2004 (Kim Ae-Ran et al., The prevalence of pullorum disease-fowl typhoid in grandparent stock and parent stock in Korea, 2003, Korean J Vet Res (2006) 46(4): 347~353). Its efficacy is doubtful, and the live vaccine is not allowed to be used for layers because of the risk of egg-transmitted infections. Unfortunately, there are still no commercially available preventive strategies against Pullorum disease, unlike Fowl Typhoid. Thus, there is an urgent need for new ways to prevent Fowl Typhoid and Pullorum disease.

Meanwhile, *Salmonella Enteritidis* (hereinafter, referred to as "SE") and *Salmonella Typhimurium* (hereinafter, referred to as "ST") are zoonotic pathogens, which show no host specificity, unlike SG or SP (Zoobises Report; United Kingdom 2003).

SE and ST are causative of salmonellosis in poultry, pigs, and cattle. Salmonellosis, caused by Salmonella bacteria, is an acute or chronic infection of the digestive tract in livestock, and shows the major symptoms of fever, enteritis, and septicemia, occasionally pneumonia, arthritis, abortion, and mastitis. Salmonellosis occurs worldwide, and most frequently during the summer months (T. R. Callaway et al. Gastrointestinal microbial ecology and the safety of the food supply as related to Salmonella. J Anim Sci 2008.86:E163-E172). In cattle, typical symptoms include loss of appetite, fever, dark brown diarrhea or bloody mucous in stool. The acute infection in calves leads to rapid death, and the infection during pregnancy leads to fetal death due to septicemia, resulting in premature abortion. In pigs, salmonellosis is characterized clinically by three major syndromes: acute septicemia, acute enteritis, and chronic enteritis. Acute septicemia occurs in 2~4-month-old piglets, and death usually occurs within 2~4 days after onset of symptoms. Acute enteritis occurs during the fattening period, and is accompanied by diarrhea, high fever, pneumonia, and nervous signs. Discoloration of the skin may occur in some severe cases. Chronic enteritis is accompanied by continuing diarrhea.

Once an outbreak of salmonellosis by SE and ST occurs in poultry, pigs, and cattle, it is difficult to cure only with therapeutic agents. The reasons are that Salmonella bacteria exhibit a strong resistance to various drugs and live in cells that are impermeable to antibiotics upon the occurrence of clinical symptoms. Up to now, there have been no methods for effectively treating salmonellosis caused by SE and ST, including antibiotics.

As in livestock, SE and ST cause infections in humans via livestock and their products, leading to *salmonella* food poisoning. Intake of infected, improperly cooked livestock products (e.g., meat products, poultry products, eggs and by-products) infects humans. *Salmonella* food poisoning in humans usually involves the prompt onset of headache, fever, abdominal pain, diarrhea, nausea, and vomiting. The symptoms commonly appear within 6-72 hours after the ingestion of the organism, and may persist for as long as 4-7 days or even longer (NSW+HEALTH. 2008.01.14.).

According to a report by the CDC (The Centers for Disease Control and Prevention, USA), 16% of human food poisoning outbreaks between 2005 and 2008 were attributed to *Salmo-* nella bacteria, with SE and ST responsible for 20% and 18% thereof, respectively. With respect to *salmonella* food poisoning in humans between 1973 and 1984, the implicated food vehicles of transmission were reportedly chicken (50), beef (19%), pork (7%), dairy products (6%), and turkey (9%). In 1974~1984, the bacterial contamination test on broilers during the slaughter process showed 35% or more of *salmonella* incidence. In 1983, *salmonella* was isolated in 50.6% of chicken, 68.8% of turkey, 60% of goose, 11.6% of pork, and 1.5% of beef. Further, a survey carried out in 2007 reported that *salmonella* was found in 5.5% of raw poultry meat and 1.1% of raw pork. In particular, it was revealed that SE commonly originated from contaminated egg or poultry meat, and ST from contaminated pork, poultry meat, and beef (www.cdc.gov) (Centers for Disease Control and Prevention (CDC)). For example, food poisoning caused by SE has rapidly increased in the US, Canada, and Europe since 1988, and epidemiological studies demonstrated that it was attributed to eggs or egg-containing foods (Agre-Food Safety Information Service (AGROS). Domestic and foreign food poisoning occurrence and management trend. 2008. 02). A risk assessment conducted by FAO and WHO in 2002 noted that the human incidence of salmonellosis transmitted through eggs and poultry meat appeared to have a linear relationship to the observed *Salmonella* prevalence in poultry. This means that, when reducing the prevalence of *Salmonella* in poultry, the incidence of salmonellosis in humans will fall (Salmonella control at the source; World Health Organization. International Food Safety Authorities Network (INFOSAN) Information Note No. 03/2007). Recently, fears about food safety have been spurred by outbreaks of *salmonella* from products as varied as peanuts, spinach, tomatoes, pistachios, peppers and, most recently, cookie dough (Jane Black and Ed O'Keefe. Overhaul of Food Safety Rules in the Works. *Washington Post* Staff Writers Wednesday, Jul. 8, 2009).

For these reasons, Salmonella infections must be reported in Germany (6 and 7 of the German law on infectious disease prevention, Infektionsschutzgesetz). Between 1990 and 2005 the number of officially recorded cases decreased from approximately 200,000 cases to approximately 50,000. It is estimated that every fifth person in Germany is a carrier of *Salmonella*. In the USA, there are approximately 40,000 cases of *Salmonella* infection reported each year.

Therefore, there is an urgent need to control SE and ST, which cause salmonellosis in livestock and humans. The collaborative efforts of USDA and FDA have developed a number of effective strategies to prevent salmonellosis that causes over 1 million cases of food-borne illness in the United States. Among them is a final rule, issued by the FDA, to reduce the contamination in eggs. The FDA will now require that egg producers test regularly for lethal *salmonella* during egg production, storage and shipment. As a result, an estimated 79,000 illnesses and 30 deaths due to contaminated eggs will be avoided each year (Jane Black and Ed O'Keefe. Overhaul of Food Safety Rules in the Works. *Washington Post* Staff Writers Wednesday, Jul. 8, 2009). In Denmark, conservative estimates from a cost benefit analysis comparing *Salmonella* control costs in the production sector with the overall public health costs of salmonellosis suggest that *Salmonella* control measures saved Danish society US$ 14.1 million in the year 2001 (*Salmonella* control at the source. World Health Organization. International Food Safety Authorities Network (INFOSAN) Information Note No. 03/2007).

Meanwhile, bacteriophage is a specialized type of virus that infects and destroys only bacteria, and can self-replicate only inside host bacteria. Bacteriophage consists of genetic material in the form of single or double stranded DNA or RNA surrounded by a protein shell. Bacteriophages are classified based on their morphological structure and genetic material. There are three basic structural forms of bacteriophage according to morphological structure: an icosahedral (twenty-sided) head with a tail; an icosahedral head without a tail; and a filamentous form. Based on their tail structure, bacteriophages having icosahedral head and double-stranded, linear DNA as their genetic material are divided into three families: Myoviridae, Siphoviridae, and Podoviridae, which are characterized by contractile, long noncontractile, and short noncontractile tails, respectively. Bacteriophages having an icosahedral head without a tail and RNA or DNA as their genetic material are divided based on their head shape and components, and the presence of shell. Filamentous bacteriophages having DNA as their genetic material are divided based on their size, shape, shell, and filament components (H. W. Ackermann. Frequency of morphological phage descriptions in the year 2000; Arch Virol (2001) 146:843-857; Elizabeth Kutter et al. Bacteriophages biology and application; CRC press).

During infection, a bacteriophage attaches to a bacterium and inserts its genetic material into the cell. After this a bacteriophage follows one of two life cycles, lytic or lysogenic. Lytic bacteriophages take over the machinery of the cell to make phage components. They then destroy or lyse the cell, releasing new phage particles. Lysogenic bacteriophages incorporate their nucleic acid into the chromosome of the host cell and replicate with it as a unit without destroying the cell. Under certain conditions, lysogenic phages can be induced to follow a lytic cycle (Elizabeth Kutter et al. Bacteriophages biology and application. CRC Press).

After the discovery of bacteriophages, a great deal of faith was initially placed in their use for infectious-disease therapy. However, when broad spectrum antibiotics came into common use, bacteriophages were seen as unnecessary due to a specific target spectrum. Nevertheless, the misuse and overuse of antibiotics resulted in rising concerns about antibiotic resistance and harmful effects of residual antibiotics in foods (Cislo, M et al. Bacteriophage treatment of suppurative skin infections. Arch Immunol. Ther. Exp. 1987.2:175-183; Kim sung-hun et al., Bacteriophage; New Alternative Antibiotics. Biological research information center (BRIC)). In particular, antimicrobial growth promoter (AGP), added to animal feed to enhance growth, is known to induce antibiotic resistance, and therefore, the ban of using antimicrobial growth promoter (AGP) has been recently introduced. In the European Union, the use of all antimicrobial growth promoters (AGPs) was banned from 2006. South Korea has banned the use of some AGPs from 2009, and is considering restrictions on the use of all AGPs in 2013~2015.

These growing concerns about the use of antibiotics have led to a resurgence of interest in bacteriophage as an alternative to antibiotics. Seven bacteriophages for control of *E. coli* O157:H are disclosed in U.S. Pat. No. 6,485,902 (Use of bacteriophages for control of *Escherichia coli* O157, issued in 2002). Two bacteriophages for control of various microorganisms are disclosed in U.S. Pat. No. 6,942,858 (issued to Nymox in 2005). Many companies have been actively trying to develop various products using bacteriophages. EBI food system (Europe) developed a food additive for preventing food poisoning caused by *Listeria monocytogenes*, named Listex-P100, which is the first bacteriophage product approved by the US FDA. A phage-based product, LMP-102 was also developed as a food additive against *Listeria monocytogenes*, approved as GRAS (Generally Regarded As Safe). In 2007, a phage-based wash produced by OmniLytics was developed to prevent *E. coli* 0157 contamination of beef during slaughter, approved by USDA's Food Safety and Inspection Service (FSIS). In Europe, *Clostridium sporogenes* phage NCIMB 30008 and *Clostridium tyrobutiricum* phage NCIMB 30008 were registered as a feed preservative against *Clostridium* contamination of feed in 2003 and 2005, respectively. Such studies show that research into bacteriophages for use as antibiotics against zoonotic pathogens in livestock products is presently ongoing.

However, most of the phage biocontrol studies have focused on the control of *E. coli*, *Listeria*, and *Clostridium*. *Salmonella* is also a zoonotic pathogen, and damages due to this pathogen are not reduced. As mentioned above, since SE and ST exhibit multiple drug resistance, nationwide antimicrobial resistance surveillance has been conducted in South Korea under the Enforcement Decree of the Act on the Prevention of Contagious Disease (Executive Order 16961), Enforcement ordinance of the Act on the Prevention of Contagious Disease (Ministry of Health and Welfare's Order 179), and Organization of the National Institute of Health (Executive Order 17164). Accordingly, there is a need for the development of bacteriophages to control *Salmonella*. The foregoing discussion is solely to provide background information of the invention and do not constitute an admission of prior art.

SUMMARY

One aspect of the present invention relates to an isolated bacteriophage, belonging to a morphotype group of the family Siphoviridae, with a specific bactericidal activity against one or more *Salmonella* bacteria selected from the group consisting of *Salmonella Enteritidis*, *Salmonella Typhimurium*, *Salmonella Gallinarum*, and *Salmonella Pullorum*, characterized by one of the following properties: the bacteriophage has a total genome size of 41~43 kb; the bacteriophage contains as a part of the genome thereof at least one nucleic acid sequence selected from among SEQ ID NOS. 1 to 6; and the bacteriophage has major structural proteins ranging in size from 39 to 41 kDa and from 16 to 18 kDa.

According to some embodiments, the foregoing bacteriophage may have a morphological structure composed of an isometric capsid and a long, non-contractile tail. According to some other embodiments, when PCR is performed in a presence of a primer set selected from among SEQ ID NOS. 7 and 8, SEQ ID NOS. 9 and 10, SEQ ID NOS. 11 and 12, SEQ ID NOS. 13 and 14, SEQ ID NOS. 15 and 16, and SEQ ID NOS. 17 and 18, with the genome of the bacteriophage serving as a template, each PCR product may be 500 bp~1,000 bp long.

According to still some other embodiments, the foregoing bacteriophage may show at least one of the following properties; tolerance to a range of from pH 3.0 to pH 11.0, tolerance to a heat range of from 37° C. to 70° C. and tolerance to desiccation at 37~60° C. for 0~120 min. In one embodiment, the bacteriophage may be identified by accession number KCCM11027P.

Another aspect of the present invention relates to a composition for prevention or treatment of infectious diseases caused by one or more *Salmonella* strains selected from the group consisting of *Salmonella Enteritidis*, *Salmonella Typhimurium*, *Salmonella Gallinarum*, and *Salmonella Pullorum*, comprising the foregoing bacteriophage. In one embodiment, the infectious disease may be salmonellosis and *salmonella* food poisoning when caused by *Salmonella enteritidis* or *Salmonella Typhimurium*, Fowl typhoid when caused by *Salmonella Gallinarum* and pullorum when caused by *Salmonella Pullorum*. In another embodiment, the composition may be used as an antibiotic.

Still another aspect of the present invention relates to an animal feed or drinking water, comprising the foregoing bacteriophage. Still another aspect of the present invention relates to a sanitizer and cleaner, comprising the foregoing bacteriophage.

Still another aspect of the present invention relates to a method for preventing or treating infectious diseases caused by one or more *Salmonella* strains selected from the group consisting of *Salmonella Enteritidis*, *Salmonella Typhimurium*, *Salmonella Gallinarum*, and *Salmonella Pullorum*, comprising administering the foregoing bacteriophage to animals in need thereof. In some of certain embodiments, it is related to a method for preventing or treating infectious diseases caused by one or more *Salmonella* strains selected from the group consisting of *Salmonella Enteritidis*, *Salmonella Typhimurium*, *Salmonella Gallinarum*, and *Salmonella Pullorum*, comprising administering the foregoing composition to animals in need thereof.

DETAILED DESCRIPTION OF THE EMBODIMENTS

Leading to the present invention, intensive and thorough research into bacteriophages, isolated from natural sources, which infect the poultry pathogen *salmonella*, conducted by the present inventors, aiming to overcome problems occurring upon the use of broad spectrum antibiotics, resulted in the finding that some isolated bacteriophages have a specific bactericidal activity against *Salmonella Enteritidis* (SE), *Salmonella Typhimurium* (ST), *Salmonella Gallinarum* (SG) and *Salmonella Pullorum* (SP) with no influences on beneficial bacteria, in addition to showing excellent acid- and heat-resistance and desiccation tolerance, as identified for the morphological, biochemical and genetic properties thereof, and thus that some bacteriophages are effective in the prevention and treatment of *Salmonella Enteritidis*- or *Salmonella Typhimurium*-mediated diseases, such as livestock salmonellosis and *Salmonella* food poisoning, and *Salmonella Gallinarum*- or *Salmonella Pullorum*-mediated diseases, particularly, Fowl Typhoid and Pullorum disease. Also, bacteriophages according to some embodiments of the present invention can be applied to various products for the control of *Salmonella* bacteria, including livestock feed additives, drinking water for livestock, barn sanitizers, and cleaners for meal products. It is one aspect of the present invention to provide a novel bacteriophage which has a specific bactericidal activity against one or more *Salmonella* bacteria selected from the group consisting of *Salmonella Enteritidis*, *Salmonella Typhimurium*, *Salmonella Gallinarum*, and *Salmonella Pullorum*.

It is another aspect of the present invention to provide a composition for the prevention or treatment of infectious diseases caused by one or more *Salmonella* bacteria selected from the group consisting of *Salmonella Enteritidis*, *Salmonella Typhimurium*, *Salmonella Gallinarum*, and *Salmonella Pullorum*, comprising the bacteriophage as an active ingredient.

It is a further aspect of the present invention to provide a livestock feed additive, drinking water for livestock, and a cleaner or a sanitizer, comprising the bacteriophage as an active ingredient.

It is still a further aspect of the present invention to provide a method for preventing or treating infectious diseases caused by one or more *Salmonella* bacteria selected from the group consisting of *Salmonella Enteritidis*, *Salmonella Typhimurium*, *Salmonella Gallinarum*, and *Salmonella Pullorum* using the composition comprising the bacteriophage as an active ingredient.

Having a specific bactericidal activity against one or more *Salmonella* bacteria selected from the group consisting of *Salmonella Enteritidis*, *Salmonella Typhimurium*, *Salmonella Gallinarum*, and *Salmonella Pullorum*, in addition to showing excellent acid- and heat-resistance and desiccation tolerance, novel bacteriophages according to some embodiments of the present invention is effective for the prevention and treatment of infectious diseases caused by *Salmonella Enteritidis*, *Salmonella Typhimurium*, *Salmonella Gallinarum*, or *Salmonella Pullorum*, including salmonellosis, *Salmonella* food poisoning, Fowl Typhoid and Pullorum disease, and can also be used for the control of *Salmonella Enteritidis*, *Salmonella Typhimurium*, *Salmonella Gallinarum*, and *Salmonella Pullorum*.

DESCRIPTION OF DRAWINGS

FIG. 1 is of photographs showing the formation of ΦCJ4 plaques in a lawn of *salmonella* bacteria: A: in a lawn of SE; B: in a lawn of ST; C: in a lawn of SG; D: in a lawn of SP; E: in a lawn of SA; F: in a lawn of SB; G: in a lawn of SC; H: in a lawn of SD. Plaques formed in lawns of SE, ST, SG and SP, but not in lawns of SA, SB, SC and SD.

FIG. 2 is an electron microphotograph of ΦCJ4, showing that ΦCJ4 belongs to a morphotype group of the family Siphoviridae, characterized by an isometric capsid and a long non-contractile tail;

FIG. 3 is the result of SDS-PAGE of the isolated bacteriophage ΦCJ4, in which major bands were detected at approximately 40 kDa and 17 kDa and minor bands at approximately 69 kDa, 38 kDa and 14 kDa, with See-blue plus 2 prestained-standard (Invitrogen) serving as a size marker;

FIG. 4 is the result of PFGE of the isolated bacteriophage ΦCJ4, showing the total genome size of approximately 42 kb, with a 5 kbp DNA size standard (Bio-rad) serving as a size marker;

FIG. 5 is the result of PCR, performed using each primer set for the ΦCJ4 genomic DNA: A: a 860 bp-long PCR product obtained with a primer set of SEQ ID NOS. 7 and 8; B: a 600 bp-long PCR product obtained with a primer set of SEQ ID NOS. 9 and 10; C: a 900 bp-long PCR product obtained with a primer set of SEQ ID NOS. 11 and 12; D: a 950 bp-long PCR product obtained with a primer set of SEQ ID NOS. 13 and 14; E: a 700 bp-long PCR product obtained with a primer set of SEQ ID NOS. 15 and 16; F: a 880 bp-long PCR product obtained with a primer set of SEQ ID NOS. 17 and 18;

FIG. 6 is the result of acid-resistance assay on the bacteriophage ΦCJ4, showing the number of surviving bacteriophage at pH 2.5, 3.0, 3.5, 4.0, 5.5, 6.4, 6.9, 7.4, 8.0, 9.0, 10.0 and 11.0. The bacteriophage ΦCJ4 did not lose its activity until pH 3.0, but completely lost its activity at pH 2.5 or lower, as compared to control;

FIG. 7 is the result of heat-resistance assay on the bacteriophage ΦCJ4, showing the number of surviving bacteriophage at 37, 45, 53, 60, 70 and 80° C. for 120 min. The bacteriophage ΦCJ4 maintained its activity at up to 70° C.; and FIG. 8 is the result of desiccation resistance assay on the bacteriophage ΦCJ4, performed at 60° C. for 120 min with the aid of speed vacuum dryer (SVD), in which when titer changes under the dry condition were measured in comparison with pre-drying titers, the activity was decreased about 10-fold.

FIG. 9 is a graph in which body weights of rats are plotted against time after administration with single dosages of the bacteriophage ΦCJ4. ■; male control administered with 20 mM Tris-HCl and 2 mM $MgCl_2$ mix, □; male control administered at a concentration of $1 \times 10^{12}$ pfu with ΦCJ4, ●; female control administered with 20 mM Tris-HCl and 2 mM $MgCl_2$ mix, ○; female test group administered at a concentration of $1 \times 10^{12}$ pfu with ΦCJ4. No significant changes in body weight were found even 14 days after the administration, in comparison with the control.

One embodiment of the present invention relates to a novel bacteriophage, belonging to a morphotype group of the family Siphoviridae, with a specific bactericidal activity against one or more *Salmonella* bacteria selected from the group consisting of *Salmonella Enteritidis*, *Salmonella Typhimurium*, *Salmonella Gallinarum*, and *Salmonella Pullorum*, having one of the following properties: 1) the bacteriophage has a total genome size of 41~43 kb; 2) the bacteriophage contains as a part of the genome thereof at least one nucleotide sequence selected from among SEQ ID NOS. 1 to 6; and 3) the bacteriophage has major structural proteins ranging in size from 39 to 41 kDa and from 16 to 18 kDa.

In a preferred embodiment, the bacteriophage has a total genome size of about 42 kb, and structural proteins corresponding to respective sizes of about 69 kDa, about 40 kDa, about 38 kDa, about 17 kDa and about 14 kDa. Further, the bacteriophage may contain as parts of the genome thereof nucleic acid molecules of SEQ ID NOS. 1 to 6.

Also, the bacteriophage according to some embodiments of the present invention has a morphological structure composed of an isometric capsid and a long, non-contractile tail.

The term "nucleic acid molecule", as used herein, is intended to include DNA (gDNA and cDNA) and RNA molecules. The term "nucleotides" which when joined together, make up the structural units of nucleic acid molecules, encompass natural ones and sugar- or base-modified analogues thereof.

Further, the bacteriophage according to some embodiments of the present invention shows biochemical properties of being resistant to acid, heat and desiccation.

In greater detail, the bacteriophage according to some embodiments of the present invention has excellent resistance to acid and heat so that it can survive over a wide pH range of from 3.5 to 11.0 and a heat range of from 37° C. to 70° C. With regard to the desiccation tolerance thereof, the bacteriophage can remain viable even under a high temperature and dry condition (e.g., 120 min at 60° C.). Thanks to the superiority thereof in resistance to acid, heat and desiccation, the bacteriophage according to some embodiments of the present invention can be used in a wide range of temperature and pH, finding applications in compositions and products for the prevention and treatment of livestock diseases and livestock-mediated human diseases.

When PCR is performed in the presence of a primer set selected from among SEQ ID NOS. 7 and 8, SEQ ID NOS. 9 and 10, SEQ ID NOS. 11 and 12, SEQ ID NOS. 13 and 14, SEQ ID NOS. 15 and 16, and SEQ ID NOS. 17 and 18, with the genome of the bacteriophage according to some embodiments of the present invention serving as a template, each PCR product is 500 bp~1,000 bp long. Preferably, PCR product is 500 bp~1,000 bp long, with the primer sets of SEQ ID NOS. 7 and 8, SEQ ID NOS. 9 and 10, SEQ ID NOS. 11 and 12, SEQ ID NOS. 13 and 14, SEQ ID NOS. 15 and 16, and SEQ ID NOS. 17 and 18.

According to some embodiments, a bacteriophage was isolated from a sewage sample of a chicken slaughterhouse that bacteriophage was identified as having a specific bactericidal activity against SE, ST, SG and SP and the above characteristics, and was designated as ΦCJ4 and deposited with the Korean Culture Center of Microorganisms (361-221, Honje 1, Seodaemun, Seoul) on Aug. 14, 2009 under accession number KCCM11027P.

In accordance with an example of the present invention, sewage samples were collected from chicken slaughterhouses and used to isolate therefrom bacteriophages that can lyse the host cell SG. They were also found to lyse SE, ST, SG and SP (FIG. 1). An morphological examination under an electron microscope confirmed that the bacteriophage (ΦCJ4) belongs to a morphotype of the family Siphoviridae (FIG. 2).

The bacteriophage ΦCJ4 was found to have major structural proteins with the size of 40 kDa and 17 kDa, as measured by a protein pattern analysis (FIG. 3).

Further, a genome analysis showed that ΦCJ4 has a total genome size of approximately 42 kbp (FIG. 4), with the nucleic acid molecules of SEQ ID NOS. 1 to 6 incorporated thereinto. Also, the bacteriophage was found to be of very low genetic similarity with known bacteriophages as measured by the comparison of genetic similarity with other species, indicating that the bacteriophage is a novel one. More particularly, when PCR was performed using the primer sets SEQ ID NOS. 7 and 8, SEQ ID NOS. 9 and 10, SEQ ID NOS. 11 and 12, SEQ ID NOS. 13 and 14, SEQ ID NOS. 15 and 16, and SEQ ID NOS. 17 and 18, which were designed for ΦCJ4, the resulting PCR products were 860 bp, 600 bp, 900 bp, 950 bp, 700 bp, and 880 bp in size, respectively (FIG. 5).

Also, the phage plaques (clear zones formed in a lawn of cells on soft agar due to lysis by phage) resulting from the infection of ΦCJ4 into SE, ST, SG and SP were observed to have the same size and turbidity.

ΦCJ4 was examined for stability under a wide spectrum of pH, temperature, and desiccation. The bacteriophage was observed to survive over a pH range of from 3.0 to 11.0 (FIG. 6) and a temperature range of from 37° C. to 70° C. (FIG. 7) in addition to remaining stably viable even after desiccation at high temperature (60° C. for 120 min) (FIG. 8).

Also, the wild-type strains SE, ST, SG and SP were also found to fall within the host cell range of ΦCJ4.

When orally administered with ΦCJ4, rats were observed to remain unchanged in weight (FIG. 9), mortality, general symptoms and organ abnormality.

Also, a claning assay shows that the bacteriophage ΦCJ4 is found to have excellent bactericidal activity against *salmonella* strains, compared to conventional cleaners as positive controls.

These data imply that the bacteriophage ΦCJ4 and its mutantscan be applied to various products for the control of *salmonella* bacteria. In accordance with another aspect thereof, the present invention pertains to a composition for the prevention or treatment of infectious diseases caused by one or more *Salmonella* bacteria selected from the group consisting of *Salmonella enteritidis, Salmonella Typhimurium, Salmonella Gallinarum,* and *Salmonella Pullorum,* comprising the bacteriophage as an active ingredient.

Preferably, examples of the infectious diseases include salmonellosis and *Salmonella* food poisoning by *Salmonella enteritidis* or *Salmonella Typhimurium,* Fowl Typhoid by *Salmonella Gallinarum* and Pullorum disease by *Salmonella Pullorum* include, but are not limited thereto.

As used herein, the term "salmonellosis" refers to symptoms following *salmonella* infection, such as fever, headache, diarrhea, and vomiting. That is, salmonellosis is an infection with bacteria of the genus *Salmonella*, with the accompaniment of two representative symptoms: septicemia such as typhoid fever; and acute gastroenteritis such as food poisoning, enteritis, and acute bacteremia.

Having a specific bactericidal activity against *Salmonella enteritidis, Salmonella Typhimurium, Salmonella Gallinarum* and *Salmonella Pullorum* according to some embodiments, the bacteriophage can be used for preventing or treating diseases that are caused by the bacteria. In a preferred embodiment, the composition may further comprise an antibiotic.

As used herein, the term "prevention" is intended to encompass all actions for restraining or delaying disease progress through the administration of the composition. The term "treatment" in this context encompasses all actions for improving or beneficially changing the patient's condition through the administration of the composition.

According to some embodiments, the composition comprises ΦCJ4 in an amount of from $5 \times 10^2$ to $5 \times 10^{12}$ pfu/ml, and preferably in an amount of from $1 \times 10^6$ to $1 \times 10^{10}$ pfu/ml.

The composition according to some other embodiments of the present invention may further comprise a pharmaceutically acceptable vehicle, and may be formulated together with the carrier into foods, medicines, and feed additives.

As used herein, the term "pharmaceutically acceptable vehicle" refers to a carrier or diluent that neither causes significant irritation to an organism nor degrades the biological activity and properties of the administered active ingredient. For use in the formulation of the composition into a liquid preparation, a pharmaceutically acceptable vehicle must be suitable for sterilization and biocompatibility. Examples include saline, sterile water, Ringer's solution, buffered physiological saline, albumin infusion solution, dextrose solution, maltodextrin solution, glycerol, and ethanol. They may be used alone or in any combination thereof. If necessary, another conventional additive, such as antioxidants, buffers, bacteriostatic agents, etc., may be added to the composition. When combined additionally with diluents, dispersants, surfactants, binders and/and lubricants, the composition according to some embodiments of the present invention may be formulated into injections such as aqueous solutions, suspensions and emulsions, or pills, capsules, granules, or tablets.

The prophylactic or therapeutic compositions according to some embodiments of the present invention may be locally applied to afflicted areas by coating or spraying. Alternatively, the composition according to some other embodiments of the present invention may be administered through oral or parenteral routes. The parenteral routes are available for intravenous, intraperitoneal, intramuscular, subcutaneous or topical administration Depending on a variety of factors including formulations, the mode of administration, the age, weight, sex, condition and diet of the patient or animal being treated, the time of administration, the route of administration, the rate of excretion, and reaction sensitivity, the suitable dosage of the composition according to some embodiments of the present invention will vary when it is applied, sprayed or administered. It will be apparent to those skilled in the art that when the pharmaceutical composition is administered to patients, the suitable total daily dose may be determined by an attending physician or veterinarian within the scope of sound medical judgment.

Oral dosage preparations of the composition according to some embodiments of the present invention may take the form of tablets, troches, lozenges, aqueous or emulsive suspensions, powders or granules, emulsions, hard or soft capsules, syrups, or elixirs. The oral dosage forms such as tablets and capsules may comprise a binder such as lactose, saccharose, sorbitol, mannitol, starch, amylopectin, cellulose or gelatin, an excipient such as dicalcium phosphate, a disintegrant such as corn starch or sweet potato starch, a lubricant such as magnesium stearate, calcium stearate, sodium stearylfumarate, or polyethylene glycol wax. For capsules, a liquid vehicle such as lipid may be further used.

For non-oral administration, the composition according to some embodiments of the present invention may be formulated into injections via subcutaneous, intravenous, or intramuscular routes, suppositories, or sprays inhalable via the respiratory tract, such as aerosols. Injection forms may be prepared by dissolving or suspending the composition according to some other embodiments of the present invention, together with a stabilizer or a buffer, in water and loading the solution or suspension onto ampules or vial unit forms. For sprays, such as aerosols, a propellant for spraying a water-dispersed concentrate or wetting powder may be used in combination with an additive.

The term "antibiotic", as used herein, refer to a substance or compound that can be administered to animals to kill bacteria or inhibit their growth and is intended to encompass antiseptics, bactericidal agents and antibacterial agents. The animals are mammals including humans. Thanks to the advantage of being of higher specificity for Salmonella over conventional antibiotics, the bacteriophage according to some embodiments of the present invention can kill the specific pathogens without affecting beneficial bacteria. Furthermore, the bacteriophage according to some other embodiments of the present invention does not induce drug resistance so that it can be provided as a novel antibiotic with a long life cycle. In accordance with a further aspect thereof, the present invention pertains to an animal feed or drinking water, comprising the bacteriophage as an active ingredient.

Feed additive antibiotics used in the fishery and livestock industry are intended to prevent infections. However, most of the currently available feed additive antibiotics are problematic in that they are apt to induce the occurrence of resistant strains and may be transferred to humans as they remain in livestock products. The uptake of such residual antibiotics may make human pathogens resistant to antibiotics, resulting in the spread of diseases. Furthermore, many kinds of feed additive antibiotics, usually used in combination in animal feeds, may cause the emergence of multidrug-resistant strains. Therefore, the bacteriophage according to some embodiments of the present invention can be used as a feed additive antibiotic that is eco-friendly enough to be a solution to the problems.

The animal feed according to some embodiments of the present invention may be prepared by adding the bacteriophage directly or in a separate feed additive form to an animal feed. In an animal feed, the bacteriophage according to some embodiments of the present invention may take a liquid or a dry form, and preferably exist as a dried powder. In this regard, the bacteriophage according to some embodiments of the present invention may be dried by air drying, natural drying, spray drying or freeze-drying, but these drying processes do not limit the present invention. The bacteriophage according to some embodiments of the present invention may be added as powder in an amount of from 0.05 to 10% by weight, preferably in an amount of from 0.1 to 2% by weight, based on the total weight of animal feed. The animal feed may comprise other conventional additives useful for the preservation thereof for a long term, in addition to the bacteriophage according to some embodiments of the present invention.

To the feed additive according to some embodiments of the present invention may be added another non-pathogenic microorganism. The available additional microorganism may be selected from the group consisting of *Bacillus subtilis* that can produce protease, lipase and invertase, *Lactobacillus* sp. strain that can exert physiological activity and a function of decomposing under an aerobic conditions, such as in the stomach of cattle, filamentous fungi including *Aspergillus oryzae* (J Animal Sci 43:910-926, 1976) that increases the weight of domestic animals, enhances milk production and helps the digestion and absorptiveness of feeds, and yeast including *Saccharomyces cerevisiae* (J Anim Sci 56:735-739, 1983). The animal feed comprising ΦCJ4 in accordance with some embodiments of the present invention may include plant-based feeds, such as grains, nuts, food byproducts, seaweed, fiber, drug byproducts, oil, starches, meal, and grain byproducts, and animal-based feeds such as proteins, minerals, fat, single cell proteins, zooplankton, and food wastes, but is not limited thereto.

The feed additive comprising ΦCJ4 in accordance with some other embodiments of the present invention may include additives for preventing quality deterioration, such as binders, emulsifiers and preservatives, and additives for increasing utility, such as amino acids, vitamins, enzymes, probiotics, flavorings, non-protein nitrogen, silicates, buffering agents, coloring agents, extracts, and oligosaccharides, but is not limited thereto.

When supplied with drinking water containing the bacteriophage according to some embodiments of the present invention, livestock can be continuously reduced in the population of *Salmonella* bacteria in the intestine thereof livestock. As a result, *Salmonella*-free livestock can be produced.

In accordance with still a further aspect thereof, the present invention pertains to a cleaner or a sanitizer, comprising the bacteriophage as an active ingredient.

The sanitizer comprising the bacteriophage as an active ingredient is very useful for food hygiene against, for example, food poisoning. In detail, the sanitizer may be utilized not only as an agent or a food additive for preventing *salmonella* contamination, but also in the production of *salmonella*-free livestock. In order to remove Salmonellar, the sanitizer can also be sprayed over domestic sewages and applied to poultry barns, slaughterhouses, spots where livestock died, cooking spaces and cooking facilities.

Further, the cleaner comprising the bacteriophage as an active ingredient can be used on a body area of living animals, such as skin, feathers and the like, which is already or potentially contaminated with *Salmonella* bacteria.

In accordance with still another aspect, the present invention relates to a method for the prevention or treatment of infectious diseases caused by one or more *Salmonella* bacteria selected from the group consisting of *Salmonella Enteritidis, Salmonella Typhimurium, Salmonella Gallinarum,* and *Salmonella Pullorum* using the bacteriophage or the composition.

The composition according to some embodiments of the present invention may be administered in the form of a pharmaceutical formulation into animals or may be ingested as a mixture with animal feed or drinking water by animals and preferably as a mixture with animal feed. In some embodiments of the present invention, the animals include cattle, pigs, chicken, poultry and humans, but are not limited thereto.

As long as it reaches target tissues, any route, whether oral or parenteral, may be taken for administering the composition according to some embodiments of the present invention. In detail, the composition according to some certain embodiments of the present invention may be administered via oral, rectal, topical, intravenous, intraperitoneal, intramuscular, intraarterial, transdermal, intranasal, and inhalation routes.

The method for the treatment of diseases in accordance with some embodiments of the present invention comprises administering the composition according to certain some embodiments of the present invention in a therapeutically effective amount. It is apparent to those skilled in the art that the total daily dose should be determined by an attending physician or veterinarian within the scope of sound medical judgment. The therapeutically effective amount for a given patient may vary depending on various factors well known in the medical art, including the kind and degree of the response to be achieved, the patient's age, body weight, state of health, sex, and diet, time and route of administration, the secretion rate of the composition, the time period of therapy, concrete compositions according to whether other agents are used therewith or not, etc.

A better understanding of some embodiments of the present invention may be obtained through the following examples which are set forth to illustrate, but are not to be construed as limiting the present invention.

Example 1

Salmonella Bacteriophage Isolation 1-1. Bacteriophage Screening and Single Bacteriophage Isolation 50 ml of each sample from a chicken slaughterhouse, located in Suwon City, Kyeonggi Do, South Korea, and a nearby sewage disposal plant were transferred to a centrifuge tube, and centrifuged at 4000 rpm for 10 min, followed by filtering the supernatant through a 0.45 µm filter. 18 mL of the sample filtrate was mixed with 150 µl of a Salmonella Gallinarum (hereinafter referred to as "SG") shaking culture medium ($OD_{600}$=2) and 2 ml of 10× Luria-Bertani medium (hereinafter referred to as "LB medium") tryptone 10 g; yeast extract 5 g; NaCl 10 g; in a final volume of 1 L). The mixture was cultured at 37° C. for 18 hrs and then centrifuged at 4000 rpm for 10 min after which the supernatant was filtered through a 0.2 µm filter. Separately, a mixture of 3 ml of 0.7% agar (w/v) and 150 µl of the SG shaking culture medium ($OD_{600}$=2) was poured across an LB plate and allowed to solidify. Over this plate was spread 10 µl of the culture filtrate, followed by incubation for 18 hrs at 37° C. (0.7% agar was used as "top-agar" and the titration of phage lysate was performed on the top-agar, called soft agar overlay technique).

A dilution of the sample culture medium containing the phage lysate was mixed with 150 µL of an SG shaking culture medium ($OD_{600}$=2) and subjected to soft agar overlay assay to produce single plaques. Since a single plaque consisted of the same bacteriophage, one plaque was taken and dissolved in 400 µL of an SM solution (NaCl, 5.8 g; $MgSO_4 7H_2O$, 2 g; 1M Tris-Cl (pH7.5), 50 ml; $H_2O$, in a final volume of 1 L), and left for 4 hours at room temperature to isolate single bacteriophages. To amplify the isolated bacteriophage, 100 µL of the supernatant was taken from the single bacteriophage solution, mixed with 12 mL of 0.7% agar and 500 µL of an SG shaking culture medium, and subjected to a soft agar overlay assay on an LB plate (150 mm in diameter). 15 mL of an SM solution was poured to a plate in which lysis had been completed, after which the plate was gently shaken for 4 hrs at room temperature to elute the bacteriophages from the top-agar. The SM solution containing the eluted bacteriophages was recovered, and chloroform was added in an amount corresponding to 1% of the final volume, and mixed well for 10 min. After centrifugation at 4000 rpm for 10 minutes, the resulting supernatant was filtered through a 0.2 µm filter, and stored in the refrigerator until use.

1-2. Large-Scale Batches of Bacteriophage

The selected bacteriophage was cultured at a large scale using SG. SG was cultured with shaking. After an aliquot of 1.5×$10^{10}$ cfu (colony forming units) was centrifuged at 4000 rpm for 10 min, the pellet was re-suspended in 4 ml of an SM solution. Into the suspension was inoculated 7.5×$10^7$ pfu (plaque forming unit) of the bacteriophage at an MOI (multiplicity of infection) of 0.005), followed by incubation at 37° C. for 20 min. This solution was inoculated into 150 mL of an LB media in a flask, and cultured at 37° C. for 5 hrs. Chloroform was added in an amount corresponding to 1% of the final volume before the culture solution was shaken for 20 min. DNase I and RNase A were added to a final concentration of 1 µg/ml, each. The solution was left at 37° C. for 30 min. NaCl and PEG (polyethylene glycol) were added to a final concentration of 1 M and 10% (w/v), respectively and left at 4° C. for an additional 3 hrs. The solution was centrifuged at 4° C. and 12,000 rpm for 20 min to discard the supernatant. A suspension of the pellet in 5 mL of an SM solution was left at room temperature for 20 minutes and mixed well with 4 mL of chloroform. After centrifugation at 4° C. and 4000 rpm for 20 min, the supernatant was filtered through a 0.2 µm filter and then subjected to ultracentrifugation using a glycerol density gradient to purify ΦCJ4 (density: 40%, 5% glycerol at 35,000 rpm and 4° C. for 1 hr). The purified ΦCJ4 was re-suspended in 300 µL of an SM solution, followed by titration. ΦCJ4 was deposited with the Korean Culture Center of Microorganisms (361-221, Honje 1, Seodaemun, Seoul) on Aug. 14, 2009 under accession number KCCM11027P.

Example 2

Examination on ΦCJ4 Infection of Salmonella

To analyze the selected bacteriophage for lytic activity on Salmonella species other than SG, attempts were made of cross infection with other Salmonella species. As a result, ΦCJ4 did not infect SC (Salmonella enterica Serotype Choleraesuis), SD (Salmonella enterica Serotype Derby), SA (Salmonella enterica sub sp. Arizonae), and SB (Salmonella enterica sub sp. Bongori), but infected SE (Salmonella Enteritidis), ST (Salmonella Typhimurium), SG (Salmonella Gallinarum) and SP (Salmonella Pullorum) (see Example 12). The results are summarized in Table 1, below and shown in FIG. 1.

TABLE 1

| ΦCJ4 Infection of Salmonella | | | | | |
|---|---|---|---|---|---|
| Sero type | Strain name | Plaque formation | Sero type | Strain name | Plaque formation |
| SE | SGSC 2282 | ○ | SA | ATCC 13314 | X |
| ST | ATCC 14028 | ○ | SB | ATCC 43975 | X |
| SG | SGSC 2293 | ○ | SC | ATCC 10708 | X |
| SP | SGSC 2295 | ○ | SD | ATCC 6960 | X |

ATCC: The Global BioresourceCenter
SGSC: Salmonella Genetic Stock Center

Example 3

Morphology of Bacteriophage ΦCJ4

The purified ΦCJ4 was diluted in a 0.01% gelatin solution, and then fixed in a 2.5% glutaraldehyde solution. The sample was dropped onto a carbon-coated mica plate (ca. 2.5×2.5 mm), adapted for 10 min, and washed with sterile distilled water. A carbon film was mounted on a copper grid, stained with 4% uranyl acetate for 30-60 sec, and dried. Examination under a JEM-1011 transmission electron microscope (at 80 kV, magnification of ×120,000~×200,000) had it that the purified ΦCJ4 consisted morphologically of an isometric capsid and a long non-contractile tail, indicating that it belongs to a morphotype group of the family Siphoviridae.

Example 4

Protein Pattern Analysis of ΦCJ4

15 μL of a ΦCJ3 solution purified at a titer of $10^{11}$ pfu/ml was mixed with 3 μL of a 5×SDS sample solution, and heated for 5 min. The total protein of ΦCJ4 was run on 4~12% NuPAGE Bis-Tris gel (Invitrogen). Then, the gel was stained with Coomassie blue for 1 hr at room temperature. Major bands were detected at 40 kDa and 17 kDa with the appearance of other bands at 69 kDa, 38 kDa and 14 kDa, as shown in FIG. 3.

Example 5

Total Genomic DNA Size of ΦCJ4

Genomic DNA of ΦCJ4 was isolated using ultracentrifugation. In this regard, to a purified ΦCJ4 culture medium were added EDTA (ethylenediaminetetraacetic acid (pH8.0)), proteinase K, and SDS (sodium dodecyl sulfate) at a final concentration of 20 mM, 50 ug/ml, and 0.5% (w/v), respectively, followed by incubation at 50° C. for 1 hr. An equal volume of phenol (pH 8.0) was added and mixed well. After centrifugation at 12,000 rpm and room temperature for 10 min, the supernatant was mixed well with an equal volume of PCI (phenol:chloroform:isoamylalhocol=25:24:1). Another centrifugation at 12,000 rpm and room temperature for 10 min produced a supernatant which was then mixed with ⅒ volume of 3 M sodium acetate and two volumes of cold 95% ethanol, and left at −20° C. for 1 hr. After centrifugation at 0° C. and 12,000 rpm for 10 min, the supernatant was completely removed, and the DNA pellet was dissolved in 50 μL of TE (Tris-EDTA (pH 8.0)). The extracted DNA was diluted 10-fold, and measured for absorbance at $OD_{260}$ to determine its concentration 1 μg of the total genomic DNA was loaded onto 1% PFGE (pulse-field gel electrophoresis) agarose gel and electrophoresed at room temperature for 20 hrs with the aid of a BIO RAD PFGE system program 7 (size range 25-100 kbp; switch time ramp 0.4-2.0 seconds, linear shape; forward voltage 180 V; reverse voltage 120V). As shown in FIG. 4, the genomic DNA of ΦCJ4 was approximately 42 kb long.

Example 6

Genetic Analysis of ΦCJ4

The genetic analysis of the purified ΦCJ4 started with triple digesting 1 μg of the genomic DNA of ΦCJ4 with the restriction enzymes, EcoR V, Sca I and Nru I. Separately, another triple digestion was performed with the restriction enzymes StuI, PvuII, and HincII. The vector pCL1920 (Promega) was digested with Sma I, and treated with CIP (calf intestinal alkaline phosphatase). The digested genomic DNA was mixed at a ratio of 3:1 with the vector, and ligated at 16° C. for 5 hrs. The resulting recombinant vector was transformed into *E. coli* DH5α which was then plated on an LB plate containing kanamycin and X-gal (5-bromo-4-chloro-3-indolyl-beta-D-galactopyranoside) for blue/white selection. The selected colonies were cultured for 16 hrs in a culture medium containing kanamycin with shaking. Then, plasmids were extracted using a plasmid purification kit (Promega).

The cloning of the plasmids was confirmed by PCR using a primer set of FRT135 and FRT136 (SEQ ID NOS. 19 and 20, respectively), and selection was made only of insert fragments having a size of 1 kb or longer. Their base sequences were analyzed using the primer set of FRT135 and FRT136 (SEQ ID NOS. 19 and 20, respectively). The base sequences thus obtained were given in SEQ ID NOS. 1 to 6, respectively, and analyzed for sequence similarity with the aid of a NCBI blastx program, and the results are summarized in Table 2, below.

TABLE 2

Sequence Similarity between ΦCJ4 and Other Bacteriophages

| No | organism | protein | Accession number | Subject location | Query location | Identity | E value |
|----|----------|---------|------------------|------------------|----------------|----------|---------|
| 1 | Salmonella phage KS7 | hypothetical protein BPKS7gp56 | YP_308656 | 187-528 | 3-1022 | 286/347 (82%) | 6e-124 |
| 2 | Salmonella phage KS7 | hypothetical protein BPKS7gp41 | YP_224063.1 | 1-212 | 80-715 | 202/212 (95%) | 1e-94 |
|   | Salmonella phage SETP3 | DNA polymerase | YP_001110810 | 1-212 | 80-715 | 198/212 (93%) | 4e-91 |
| 3 | Salmonella phage KS7 | hypothetical protein BPKS7gp56 | YP_308656 | 187-479 | 3-881 | 274/293 (93%) | 3e-139 |
| 4 | Salmonella phage KS7 | hypothetical protein BPKS7gp50 | YP_224072 | 1-180 | 540-1 | 172/180 (95%) | 5e-95 |
|   | Salmonella phage SETP3 | tailspike protein | YP_001110804 | 1-180 | 540-1 | 171/180 (95%) | 3e-94 |
|   | Salmonella phage SETP3 | tail component protein | YP_001110803 | 467-598 | 951-556 | 124/132 (93%) | 1e-66 |
|   | Salmonella phage KS7 | hypothetical protein BPKS7gp51 | YP_224073 | 578-709 | 951-556 | 122/132 (92%) | 3e-65 |
| 5 | Salmonella phage KS7 | hypothetical protein BPKS7gp57 | YP_308657 | 1-96 | 567-854 | 95/96 (98%) | 8e-56 |
|   | Salmonella phage KS7 | hypothetical protein BPKS7gp58 | YP_308658 | 1-78 | 196-429 | 77/78 (98%) | 1e-13 |

TABLE 2-continued

Sequence Similarity between ΦCJ4 and Other Bacteriophages

| No | organism | protein | Accession number | Subject location | Query location | Identity | E value |
|---|---|---|---|---|---|---|---|
| 6 | *Salmonella* phage SETP3 | tail component protein | YP_001110803 | 201-531 | 1-993 | 324/331 (97%) | 6e-124 |
| | *Salmonella* phage KS7 | hypothetical protein BPKS7gp51 | YP_224073 | 312-642 | 1-993 | 322/331 (97%) | 1e-123 |

Example 7

Design of ΦCJ4-Specific Primer Sequences

In order to identify ΦCJ4, ΦCJ4-specific primers were designed on the basis of SEQ ID NOS. 1 to 6. PCR was performed using each primer set of SEQ ID NOS. 7 and 8, SEQ ID NOS. 9 and 10, SEQ ID NOS. 11 and 12, SEQ ID NOS. 13 and 14, SEQ ID NOS. 15 and 16 and SEQ ID NOS. 17 and 18. 0.1 μg of the genomic DNA of bacteriophage and 0.5 pmol of each primer were added to pre-mix (Bioneer), and the final volume was adjusted to 20 μL. PCR was performed with 30 cycles of denaturation; 94° C. 30 sec, annealing; 60° C. 30 sec, and polymerization; 72° C., 1 min. The PCR products thus obtained were approximately 860 bp, 600 bp, 900 bp, 950 bp, 700 bp, and 880 bp long, respectively, with the primer sets of SEQ ID NOS. 7 and 8, SEQ ID NOS. 9 and 10, SEQ ID NOS. 11 and 12, SEQ ID NOS. 13 and 14, SEQ ID NOS. 15 and 16 and SEQ ID NOS. 17 and 18. The results are shown in FIG. 5.

Example 8 pH Stability of Bacteriophage

In order to determine whether ΦCJ4 survives the low pH environment in the stomach of livestock, ΦCJ4 was assayed for stability in a wide range of pH (pH 2.5, 3.0, 3.5, 4.0, 5.5, 6.4, 6.9, 7.4, 8.2, 9.0, 10.0, 11.0). Various pH solutions (sodium acetate buffer (pH 4.0, pH 5.5, pH 6.4), sodium citrate buffer (pH 2.5, pH 3.0, pH 3.5), sodium phosphate buffer (pH 6.9, pH 7.4) and Tris-HCl (pH 8.2, pH 9.0, pH 10.0, pH 11.0)) were prepared to have a concentration of 2 M. 180 μL of each pH solution was mixed with 20 μL of a bacteriophage solution ($1.0 \times 10^{10}$ pfu/ml), followed by incubation at room temperature for 2 hr. The reaction solution was serially diluted, and 10 μL of each dilution was cultured at 37° C. for 18 hrs by a soft agar overlay method to determine the titers of the phage lysates. Titer changes with pH were measured to determine the stability of bacteriophage over pH in comparison to titers of ΦCJ4 at 0 hr. The results showed that the bacteriophage did not lose its activity and remained stable down to pH 3.5. The results are shown in FIG. 6.

Example 9

Heat Stability of Bacteriophage

For use as a feed additive, the bacteriophage was assayed for stability to the heat generated during a formulation process. In this regard, 200 μL, of a ΦCJ4 solution with a titer of $1.0 \times 10^{10}$ pfu/ml was incubated at 37° C., 45° C., 53° C., 60° C., 70° C., or 80° C. for 2 hr. The solution was serially diluted, and 10 μL, of each dilution was cultured at 37° C. for 18 hrs by a soft agar overlay method to determine the titers of phage lysates. Titer changes with temperature and exposure time were measured to determine the stability of bacteriophage to heat in comparison to titers at 0 hr and 37° C. The results showed that the bacteriophage did not lose its activity at 70° C. for up to 2 hrs, but was deactivated at 80° C. or higher. The results are shown in FIG. 7.

Example 10

Desiccation Tolerance of Bacteriophage

For use as a feed additive, the bacteriophage was assayed for tolerance to the dry condition set for a formulation process. On the basis of the results obtained from the heat stability assay, an assay was performed at 60° C. for 2 hr as follows. 200 μL of a ΦCJ4 solution ($1.0 \times 10^{11}$ pfu/ml) was dried using a Speed vacuum (Speed-Vacuum Concentrator 5301, Eppendorf). The pellet thus obtained was completely re-suspended overnight at 4° C. in an equal volume of an SM solution. The solution was serially diluted, and 10 μL of each dilution was cultured at 37° C. for 18 hrs using a soft agar overlay method to determine the titers of phage lysates. Titer changes under the dry condition were measured to determine the desiccation tolerance of the bacteriophage in comparison with pre-drying titers. The results showed that its activity was decreased about 10-fold. The results are shown in FIG. 8.

Example 11

Spectrum of Wile-Type Host Cell Strains to which Bacteriophage Infects

ΦCJ4 was assayed for lytic activity against Korean wild-type SE (38 strains), ST (22 strains), SG (56 strains) and SP (19 strains), obtained from Laboratory of Avian Diseases, College of Veterinary Medicine, Seoul National University, and National Veterinary Research and Quarantine Service and the Korea Centers for Disease Control and Prevention, in addition to the strains used in at least some embodiments of the present invention, SE (SE SCSG 2282), ST (ST ATCC14028), SG (SG SGSC2293) and SP (SP SGSC2295). 150 μL of each strain shaking culture medium ($OD_{600}=2$) was mixed, and 10 μL of ΦCJ4 solution ($10^{10}$ pfu/ml) was cultured at 37° C. for 18 hrs using a soft agar overlay method to monitor the formation of plaques. It was observed that the bacteriophage ΦCJ4 showed lytic activity of 97% against SE, 91% against ST, 96% against SG and 85% against SP. The results are summarized in Table 3, below.

TABLE 3

Lytic Activity of ΦCJ4 against Korean Wild-Type Strains SE, ST, SG, and SP

| Sero-type | Strain name | Plaque formation | Sero-type | Strain name | Plaque formation |
|---|---|---|---|---|---|
| SG | SNU SG1 | ○ | ST | SNU ST1 | ○ |
| | SNU SG2 | ○ | | SNU ST2 | ○ |

TABLE 3-continued

Lytic Activity of ΦCJ4 against Korean Wild-Type Strains SE, ST, SG, and SP

| Sero-type | Strain name | Plaque formation | Sero-type | Strain name | Plaque formation |
|---|---|---|---|---|---|
| | SNU SG3 | ○ | | SNU ST3 | ○ |
| | SNU SG4 | ○ | | SNU ST4 | ○ |
| | SNU SG5 | ○ | | SNU ST7 | ○ |
| | SNU SG6 | ○ | | SNU ST8 | ○ |
| | SNU SG7 | ○ | | SNU ST11 | ○ |
| | SNU SG8 | ○ | | SNU ST12 | ○ |
| | SNU SG9 | ○ | | SNU ST13 | ○ |
| | SNU SG10 | ○ | | SNU ST14 | ○ |
| | SNU SG11 | ○ | | SNU ST17 | ○ |
| | SNU SG12 | ○ | | SNU ST18 | X |
| | SNU SG13 | ○ | | SNU ST19 | X |
| | SNU SG14 | ○ | | SNU ST20 | ○ |
| | SNU SG15 | ○ | | SNU ST25 | ○ |
| | SNU SG16 | ○ | | SNU ST26 | ○ |
| | SNU SG17 | ○ | | SNU ST37 | ○ |
| | SNU SG18 | ○ | | SNU ST38 | ○ |
| | SNU SG19 | ○ | | SNU ST41 | ○ |
| | SNU SG20 | ○ | | SNU ST42 | ○ |
| | SNU SG21 | ○ | | ATCC UK1 | ○ |
| | SNU SG22 | ○ | | ATCC 14028S | ○ |
| | SNU SG23 | ○ | | SGSC STM1412 | ○ |
| | SNU SG24 | ○ | | SGSC STM260 | ○ |
| | SNU SG25 | ○ | | SGSC STM SA2197 | ○ |
| | SNU SG26 | ○ | SE | SGSC SE2282 | ○ |
| | SNU SG27 | ○ | | SGSC SE2377 | ○ |
| | SNU SG28 | ○ | | PT4 S1400194 | ○ |
| | SNU SG30 | ○ | | PT4 LA52 | ○ |
| | SNU SG31 | ○ | | NVRQS SE004 | ○ |
| | SNU SG32 | ○ | | NVRQS SE005 | ○ |
| | SNU SG33 | ○ | | KCDC SE008 | ○ |
| | SNU SG34 | ○ | | KCDC SE009 | ○ |
| | SNU SG36 | ○ | | KCDC SE010 | ○ |
| | SNU SG37 | ○ | | KCDC SE011 | X |
| | SNU SG38 | ○ | | KCDC SE012 | ○ |
| | SNU SG39 | ○ | | KCDC SE013 | ○ |
| | SNU SG40 | ○ | | KCDC SE014 | ○ |
| | SNU SG41 | ○ | | KCDC SE015 | ○ |
| | SNU SG42 | ○ | | KCDC SE016 | ○ |
| | SNU SG43 | ○ | | KCDC SE017 | ○ |
| | SNU SG44 | ○ | | KCDC SE018 | ○ |
| | SNU SG45 | ○ | | KCDC SE019 | ○ |
| | SNU SG46 | ○ | | KCDC SE020 | ○ |
| | SNU SG47 | ○ | | KCDC SE021 | ○ |
| | SNU SG48 | ○ | | KCDC SE022 | ○ |
| | SNU SG49 | ○ | | KCDC SE023 | ○ |
| | SNU SG50 | ○ | | KCDC SE024 | ○ |
| | SGSC SG9184 | ○ | | KCDC SE025 | ○ |
| | SGSC SG2292 | ○ | | KCDC SE026 | ○ |
| | SGSC SG2293 | ○ | | KCDC SE027 | ○ |
| | SGSC SG2744 | ○ | | KCDC SE028 | ○ |
| | SGSC SG2796 | ○ | | KCDC SE029 | ○ |
| SP | SNU SP1 | ○ | | KCDC SE030 | ○ |
| | SNU SP4 | ○ | | KCDC SE031 | ○ |
| | SNU SP5 | ○ | | KCDC SE032 | ○ |
| | SNU SP8 | ○ | | KCDC SE033 | ○ |
| | SNU SP11 | ○ | | KCDC SE034 | ○ |
| | SGSC SP2294 | ○ | | KCDC SE035 | ○ |
| | SGSC SP2295 | ○ | | KCDC SE036 | ○ |
| | SGSC SP2737 | X | | KCDC SE037 | ○ |
| | SGSC SP2739 | X | SC | ATCC SC10708 | X |
| | SGSC SP2742 | ○ | | ATCC SC2929 | X |
| | SGSC SP2743 | ○ | SD | ATCC SD6960 | X |
| | SGSC SP2745 | ○ | | ATCC SD2466 | ○ |
| | SGSC SP2751 | ○ | | ATCC SD2467 | ○ |
| | SGSC SP4663 | X | | ATCC SD2468 | X |
| | SGSC SP4664 | ○ | SA | ATCC SA13314 | X |
| | SGSC SP4665 | ○ | SB | ATCC SB43975 | X |
| | SGSC SP4666 | ○ | | | |
| | SGSC SP4667 | ○ | | | |
| | SGSC SA1684 | ○ | | | |

SNU: Laboratory of Avian Diseases, College of Veterinary Medicine, Seoul National University
SGSC: *salmonella* genetic stock center
NVRQS: National Veterinary Research & Quarantine Service
KCDC: Korean Centers for Disease Control and prevention
ATCC: The Global BioresourceCenter Example 12

Toxicity Assay of Bacteriophage

For safety use in the prevention of salmonellosis, *salmonella* food poisoning, fowl typhoid and pullorum, the bacteriophage was in vivo assayed for toxicity. Toxicity assay was performed with single oral dosages. In this assay, rats were orally administered with a single dosage of ΦCJ4 and monitored for acute toxicity to determine approximate lethal concentrations of ΦCJ4. To this end, first, specific-pathogen free (SPF) male and female rats (SD) 7 weeks old, each of 10, were starved for 24 hrs before administration with ΦCJ4. On the administration day, five males and five females were orally administered at a dose of 10 mL/kg with ΦCJ4 having a titer of $1 \times 10^{12}$ pfu/ml using an oral sonde while five controls were orally administered with a 20 mM Tris-HCl and 2 mM $MgCl_2$ mix. Four hrs after the oral administration, feeds were provided for rats. Monitoring was conducted every hour for 4 hours, starting from 30 min after the administration on the day of administration. Since then, they were monitored once a day for 14 days for general symptoms. None of them died. Neither toxic symptoms nor noticeable clinical symptoms were generated by ΦCJ4. The results are summarized in Tables 4 and 5, below. Body weights were recorded before and 1 3, 7, 10 and 14 days after administration. No significant changes were observed in body weight, indicating that ΦCJ4 does not cause a toxic reaction sufficient to reduce appetite or to change the body weight. These results are shown in FIG. 9. No noticeable abnormalities were found in any organ as examined by autopsy and with the naked eye. Therefore, the novel bacteriophage ΦCJ4 is non-toxic.

TABLE 4

Oral Toxicity Assay of ΦCJ4 in Terms of Mortality

| | | Done | Hours after treatment | | | | | Days after treatment | | | | | | | | | Final |
|---|---|---|---|---|---|---|---|---|---|---|---|---|---|---|---|---|---|
| Sex | | (Pfu/kg) | 0.5 | 1 | 2 | 3 | 4 | 5 | 6 | 7 | 8 | 9 | 10 | 11 | 12 | 13 | 14 | Mortality |
| Male | | Control | 0 | 0 | 0 | 0 | 0 | 0 | 0 | 0 | 0 | 0 | 0 | 0 | 0 | 0 | 0 | 0/5 |
| | | $10^{13}$ | 0 | 0 | 0 | 0 | 0 | 0 | 0 | 0 | 0 | 0 | 0 | 0 | 0 | 0 | 0 | 0/5 |

TABLE 4-continued

Oral Toxicity Assay of ΦCJ4 in Terms of Mortality

| Sex | Done (Pfu/kg) | Hours after treatment | | | | | | | | Days after treatment | | | | | | Final Mortality |
|---|---|---|---|---|---|---|---|---|---|---|---|---|---|---|---|---|
| | | 0.5 | 1 | 2 | 3 | 4 | 5 | 6 | 7 | 8 | 9 | 10 | 11 | 12 | 13 | 14 | |
| Female | control | 0 | 0 | 0 | 0 | 0 | 0 | 0 | 0 | 0 | 0 | 0 | 0 | 0 | 0 | 0 | 0/5 |
| | $10^{13}$ | 0 | 0 | 0 | 0 | 0 | 0 | 0 | 0 | 0 | 0 | 0 | 0 | 0 | 0 | 0 | 0/5 |

TABLE 5

Oral Toxicity Assay of ΦCJ4 in Terms of General Symptoms

| Sex | Done Pfu/kg | Final Mortality Male | Female | Clinical Signs Male | Female |
|---|---|---|---|---|---|
| Male | Control | 0/5 | 0/5 | 0/5 | 0/5 |
| | $10^{13}$ | 0/5 | 0/5 | 0/5 | 0/5 |
| Female | Control | 0/5 | 0/5 | 0/5 | 0/5 |
| | $10^{13}$ | 0/5 | 0/5 | 0/5 | 0/5 |

TABLE 6

Oral Toxicity Assay of ΦCJ4 in Terms of Organ Abnormality

| Sex | Done (pfu/kg) | Gross finding | Frequency |
|---|---|---|---|
| Male | Control | N.A.D | 5/5 |
| | $10^{13}$ | N.A.D | 5/5 |
| Female | Control | N.A.D | 5/5 |
| | $10^{13}$ | N.A.D | 5/5 | a: not detected.

Example 13

Efficiency of Bacteriophage as a Cleaner

In order to evaluate the efficiency of the bacteriophage as a cleaner for meat products, the bacteriophage was assayed for ability to control *salmonella* bacteria in comparison with a conventional cleaner. In this regard, 50 g of chicken breast cuts was purchased from a store. An ST shaking culture (O.D.=2) was adjusted to a concentration of $10^8$ cfu/ml and uniformly spread in an amount of 200 μL over the chicken breast cuts which were then dried at room temperature for 12 min. The bacteriophage ΦCJ4 and the cleaner chlorine (4~6% Sodium hypochlorite) were contained at a concentration of $10^8$ pfu/L and 50 ppm in respective sprayers and sprayed at a rate of one stroke/sec for 10 sec. The treated chicken breast cuts were placed in respective sanitary packs to which an SM buffer was then added. The packs were shaken in a semicircle pattern. The WCR (whole carcass rinse) thus obtained was serially diluted and the dilutions were spread over LB media, followed by incubation at 37° C. for 18 hrs to determine the number of ST. When treated with the bacteriophage ΦCJ4, the population of ST was 24.29% reduced. In contrast, the cleaner was observed to induce *salmonella* bacteria to increase 14%. Accordingly, the bacteriophage ΦCJ4 has cleaning activity far better than that of the conventional cleaner. The results are given in Table 7, below.

TABLE 7

Comparison of Cleaning Efficiency between ΦCJ4 and Cleaner

| | Substance | Reduction Rate of *Salmonella* (%) |
|---|---|---|
| 1 | SM buffer | |
| 2 | Chlorine 50 ppm | (+14.50) |
| 3 | ΦCJ4 $2.0 \times 10^8$ pfu/L | 24.49 |

Having specific bactericidal activity against one or more *Salmonella* bacteria selected from the group consisting of *Salmonella Enteritidis* (SE), *Salmonella Typhimurium* (ST), *Salmonella Gallinarum* (SG), and *Salmonella Pullorum* (SP) without affecting beneficial bacteria, in addition to showing excellent tolerance to acid, heat and desiccation, as described hitherto, the novel bacteriophage according to some embodiments of the present invention can be widely used as an active ingredient for therapeutic agents, animal feeds or drinking water, cleaners and sanitizers for preventing and treating the infectious diseases caused by *Salmonella Enteritidis, Salmonella Typhimurium, Salmonella Gallinarum* or *Salmonella Pullorum* including salmonellosis, *Salmonella* food poisoning, Fowl Typhoid, and Pullorum disease.

Although preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An isolated bacteriophage having a specific bactericidal activity against one or more *Salmonella* bacteria selected from the group consisting of *Salmonella Enteritidis, Salmonella Typhimurium, Salmonella Gallinarum*, and *Salmonella Pullorum*, which is deposited under accession number KCCM11027P.

2. A composition for prevention or treatment of infectious diseases caused by one or more *Salmonella* bacteria selected from the group consisting of *Salmonella Enteritidis, Salmonella Typhimurium, Salmonella Gallinarum*, and *Salmonella Pullorum*, comprising the bacteriophage of claim 1.

3. The composition according to claim 2, wherein the infectious diseases are salmonellosis and salmonella food poisoning caused by *Salmonella enteritidis* or *Salmonella Typhimurium*, Fowl typhoid caused by *Salmonella Gallinarum* and pullorum caused by *Salmonella Pullorum*.

4. An antibiotic composition comprising an isolated bacteriophage having a specific bactericidal activity against one or more *Salmonella* bacteria selected from the group consisting of *Salmonella Enteritidis, Salmonella Typhimurium, Salmonella Gallinarum*, and *Salmonella Pullorum*, which is deposited under accession number KCCM11027P.

5. An animal feed or drinking water, comprising the bacteriophage of claim 1.

6. A sanitizer and cleaner, comprising the bacteriophage of claim 1.

7. A method for treating infectious diseases caused by one or more *Salmonella* bacteria selected from the group consisting of *Salmonella Enteritidis, Salmonella Typhimurium, Salmonella Gallinarum*, and *Salmonella Pullorum*, comprising administering the bacteriophage of claim 1 to animals in need thereof.

8. A method for treating infectious diseases caused by one or more *Salmonella* bacteria selected from the group consisting of *Salmonella Enteritidis, Salmonella Typhimurium, Salmonella Gallinarum*, and *Salmonella Pullorum*, comprising administering the composition of claim 2 to animals in need thereof.

* * * * *